(12) United States Patent
Thomas et al.

(10) Patent No.: US 11,180,758 B2
(45) Date of Patent: Nov. 23, 2021

(54) ANTIVIRAL PROTEINS AND THEIR USES IN THERAPEUTIC METHODS

(71) Applicant: THE JOHNS HOPKINS UNIVERSITY, Baltimore, MD (US)

(72) Inventors: David Lee Thomas, Lutherville, MD (US); Ashwin Balagopal, Columbia, MD (US); Ramy El-Diwany, Baltimore, MD (US); Robert Siliciano, Baltimore, MD (US); Joel Blankson, Baltimore, MD (US); Stuart C Ray, Lutherville, MD (US); Michel Anand Chattergoon, Baltimore, MD (US); Justin Bailey, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 317 days.

(21) Appl. No.: 16/078,760

(22) PCT Filed: Feb. 24, 2017

(86) PCT No.: PCT/US2017/019277
§ 371 (c)(1),
(2) Date: Aug. 22, 2018

(87) PCT Pub. No.: WO2017/147370
PCT Pub. Date: Aug. 31, 2017

(65) Prior Publication Data
US 2019/0085333 A1 Mar. 21, 2019

Related U.S. Application Data

(60) Provisional application No. 62/299,086, filed on Feb. 24, 2016.

(51) Int. Cl.
| | |
|---|---|
| *C12N 15/12* | (2006.01) |
| *A61K 38/00* | (2006.01) |
| *C12N 15/113* | (2010.01) |
| *A61K 38/45* | (2006.01) |

(Continued)

(52) U.S. Cl.
CPC .......... *C12N 15/1132* (2013.01); *A61K 38/00* (2013.01); *A61K 38/1709* (2013.01); *A61K 38/45* (2013.01); *A61P 31/18* (2018.01); *C12Y 207/00* (2013.01)

(58) Field of Classification Search
CPC ............ A61K 39/21; A61K 2039/5256; A61K 39/12; A61K 2039/5258; A61K 38/00; A61K 2300/00; A61K 35/17; A61K 45/06; A61K 39/00; A61K 31/00; A61K 38/1793; A61K 38/18; A61K 38/19; A61K 38/20; A61K 39/001116; A61K 39/001119; C07K 14/705; C07K 16/1063; C07K 2317/622; C07K 14/4747; C12N 15/85; C12N 15/86; C12N 2740/13023; C12N 2740/13034; C12N 2740/15023; C12N 2740/15034; C12N 2740/16043; C12N 2760/16023; C12N 2760/16034; C12N 2760/16134; C12N 2760/16143; C12N 2310/14; C12N 15/1132; A61P 31/18; A61P 35/00; A61P 11/02; A61P 11/06; A61P 11/16; A61P 15/00; A61P 15/08; A61P 15/12; A61P 15/14; A61P 17/00; A61P 17/02; A61P 17/08; A61P 17/12; A61P 17/14; A61P 19/02; A61P 19/08; A61P 19/10; A61P 1/02; A61P 1/04; A61P 1/08; A61P 1/14; A61P 1/16; A61P 21/02; A61P 21/04; A61P 25/00; A61P 25/02; A61P 25/04; A61P 25/06; A61P 25/08; A61P 25/12; A61P 25/14; A61P 25/16; A61P 25/18; A61P 25/20; A61P 25/22; A61P 25/24; A61P 25/28; A61P 25/30; A61P 25/32; A61P 25/34; A61P 25/36; A61P 27/02; A61P 27/16; A61P 29/00; A61P 31/04; A61P 31/22; A61P 35/02; A61P 37/00; A61P 37/08; A61P 3/04; A61P 3/06; A61P 3/10; A61P 3/12; A61P 3/14; A61P 43/00; A61P 5/00; A61P 5/06; A61P 5/38; A61P 5/50; A61P 7/00; A61P 7/04; A61P 9/00; A61P 9/04; A61P 9/06; A61P 9/10; A61P 9/12;
(Continued)

(56) References Cited

U.S. PATENT DOCUMENTS

| | | |
|---|---|---|
| 5,166,050 A | 11/1992 | Shriver et al. |
| 5,399,363 A | 3/1995 | Liversidge et al. |
| 5,466,468 A | 11/1995 | Schneider et al. |

(Continued)

FOREIGN PATENT DOCUMENTS

WO  2008134046 A1  11/2008

OTHER PUBLICATIONS

Wahl et al., Molecular Hybridization of Immobilized Nucleic Acids: Theoretical Concepts and Practical Considerations., (1987) Methods Enzymol. 152:399.

(Continued)

*Primary Examiner* — Bao Q Li
(74) *Attorney, Agent, or Firm* — JH Technology Ventures

(57) ABSTRACT

Three proteins, BCL-G (BCL2L14), CMPK2, and LAMP3, were discovered to independently restrict HIV-1 replication both in-vivo and in-vitro. Methods are described wherein subjects are given an effective amount of a pharmaceutical composition comprising a protein selected from the group consisting of BCL-G, CMPK2, LAMP3, functional parts thereof, recombinant proteins thereof, and combinations thereof, for the purpose of treating or preventing HIV.

5 Claims, 5 Drawing Sheets
Specification includes a Sequence Listing.

(51) Int. Cl.
*A61K 38/17* (2006.01)
*A61P 31/18* (2006.01)

(58) Field of Classification Search
CPC ... A61P 9/14; C07C 323/25; C12Q 2600/158; G16B 5/00
See application file for complete search history.

(56) References Cited

U.S. PATENT DOCUMENTS

| | | | |
|---|---|---|---|
| 5,543,158 | A | 8/1996 | Gref et al. |
| 5,580,579 | A | 12/1996 | Ruddy et al. |
| 5,629,001 | A | 5/1997 | Michael et al. |
| 5,641,515 | A | 6/1997 | Ramtoola |
| 5,725,871 | A | 3/1998 | Illum |
| 5,756,353 | A | 5/1998 | Debs |
| 5,780,045 | A | 7/1998 | McQuinn et al. |
| 5,792,451 | A | 8/1998 | Sarubbi et al. |
| 5,804,212 | A | 9/1998 | Ilium |
| 6,613,308 | B2 | 9/2003 | Bartus et al. |
| 6,737,514 | B1 | 5/2004 | Wang et al. |
| 7,638,324 | B2 | 12/2009 | Reed et al. |
| 2007/0072831 | A1 | 3/2007 | Cai et al. |

OTHER PUBLICATIONS

Kimmel., Identification and characterization of specific clones: Strategy for confirming the validity of presumptive clones., (1987) Methods Enzymol. 152:507.
Mathiowitz et al., 1997 Biologically erodable microspheres as potential oral drug delivery systems., Nature 386 (6623):410-4.
Takenaga et al., 1998 Microparticle resins as a potential nasal drug delivery system for insulin., J Control Release 52:81-7.
Langevin et al., The antiviral innate immune response in fish: evolution and conservation of the IFN system. J. Mol. Biol. 425, 4904-4920 (2013).
Sandler et al., Type I interferon responses in rhesus macaques prevent SIV infection and slow disease progression. Nature 511, 601-605 (2014).
Goujon et al., Characterization of the alpha interferon-induced postentry block to HIV-1 infection in primary human macrophages and T cells. J. Virol. 84, 9254-9266 (2010).
Bosinger et al., Global genomic analysis reveals rapid control of a robust innate response in SIV-infected sooty mangabeys. J. Clin. Invest. 119, 3556-3572 (2009).
Asmuth et al., Safety, tolerability, and mechanisms of antiretroviral activity of pegylated interferon Alfa-2a in HIV-1-monoinfected participants: a phase II clinical trial. J.Infect. Dis. 201, 1686-1696 (2010).
Azzoni et al., Pegylated Interferon alfa-2a monotherapy results in suppression of HIV type 1 replication and decreased cell-associated HIV DNA integration. J. Infect. Dis. 207, 213-222 (2013).
Goujon et al., Human MX2 is an interferon-induced post-entry inhibitor of HIV-1 infection. Nature 502, 559-562 (2013).
Kane et al., MX2 is an interferon-induced inhibitor of HIV-1 infection. Nature 502, 563-566 (2013).
Neil et al., Tetherin inhibits retrovirus release and is antagonized by HIV-1 Vpu. Nature 451, 425-430 (2008).
Sedaghat et al., Chronic CD4+ T-cell 511 activation and depletion in human immunodeficiency virus type 1 infection: type I interferon-mediated disruption of T-cell dynamics. J. Virol. 82, 1870-1883 (2008).
Doitsh et al., Cell death by pyroptosis drives CD4 T-cell depletion in HIV-1 infection. Nature 505, 509-514 (2014).
Wodarz et al., Mathematical models of HIV pathogenesis and treatment. BioEssays News Rev. Mol. Cell. Dev. Biol. 24, 1178-1187 (2002).

Finzi et al., Viral Dynamics in HIV-1 Infection. Cell 93, 665-671 (1998).
Perelson et al., HIV-1 dynamics in vivo: virion clearance rate, infected cell life-span, and viral generation time. Science 271, 1582-1586 (1996).
Beq et al., Altered thymic function during interferon therapy in HCV-infected patients. PloS One 7, e34326 (2012).
Katsounas et al., Differential Specificity of Interferon-alpha Inducible Gene Expression in Association with Human Immunodeficiency Virus and Hepatitis C Virus Levels and Declines in vivo. J. AIDS Clin. Res. 6, (2015).
Balagopaul et al., Antiretroviral therapy, interferon sensitivity, and virologic setpoint in human immunodeficiency virus/hepatitis C virus coinfected patients. Hepatology 60, 477-486 (2014).
Pan et al., Restrictions to HIV-1 replication in resting CD4+ T lymphocytes. Cell Res. 23, 876-885 (2013).
Zhou et al., Kinetics of human immunodeficiency virus type 1 decay following entry into resting CD4+ T cells. J. Virol. 79, 2199-2210 (2005).
Zack et al., HIV-1 entry into quiescent primary lymphocytes: molecular analysis reveals a labile, latent viral structure. Cell 61, 213-222 (1990).
Chen et al., Alpha interferon potently enhances the anti-human immunodeficiency virus type 1 activity of APOBEC3G in resting primary CD4 T cells. J. Virol. 80, 7645-7657 (2006).
Pillai et al., Role of retroviral restriction factors in the interferon-α-mediated suppression of HIV-1 in vivo. Proc. Natl. Acad. Sci. U. S. A. 109, 3035-3040 (2012).
Schoggins et al., A diverse range of gene products are effectors of the type I interferon antiviral response. Nature 472, 481-485 (2011).
Weil et al., Uracil DNA glycosylase initiates degradation of HIV-1 cDNA containing misincorporated dUTP and prevents viral integration. Proc. Natl. Acad. Sci. U. S. A. 110, E448-457 (2013).
Guo et al., BCL-G, a novel pro-apoptotic member of the Bcl-2 family. J. Biol. Chem. 276, 2780-2785 (2001).
Giam et al., Bcl-2 family member Bcl-G is not a proapoptotic protein. Cell Death Dis. 3, e404 (2012).
Harper et al., Interferon-α Subtypes in an Ex Vivo Model of Acute HIV-1 Infection: Expression, Potency and Effector Mechanisms. PLoS Pathog. 11, e1005254 (2015).
Dicks M., et al., "Oligomerization Requirements for MX2-Mediated Suppression of HIV-1 Infection" Journal of Virology, Jan. 2016 vol. 90 No. 1.
Li et al., RSEM: accurate transcript quantification from RNA-Seq data with or without a reference genome. BMC Bioinformatics 12, 323 (2011).
Leng et al., EBSeq: an empirical Bayes hierarchical model for inference in RNA-seq experiments. Bioinforma. Oxf. Engl. 29, 1035-1043 (2013).
Hochberg et al., More powerful procedures for multiple significance testing. Stat. Med. 9, 811-818 (1990).
Gunthard et al., Antiretroviral Drugs for Treatment and Prevention of HIV Infection in Adults 2016 Recommendations of the International Antiviral Society—USA Panel., JAMA 2016, 316(2):191.
Badowski et al., New Antiretroviral Treatment for HIV., Infectious Diseases and Therapy 2016, 5(3):329.
Dominguez-Bautista, J., et al., "Loss of lysosome-associated membrane protein 3 (LAMP3) enhances cellular vulnerability against proteasomal inhibition" European Journal of Cell Biology 94 (2015) 148-161.
Kambara, H., et al., "Negative regulation of the interferon response by an interferon-induced long non-coding RNA" Nucleic Acids Research, 2014, vol. 42, No. 16.
Strack, P., et al., "Apoptosis mediated by HIV protease is preceded by cleavage of Bcl-2", Proc. Natl. Acad. Sci. USA, (1996) vol. 93, pp. 9571-9576.
Database GenBank: NM_002463.1, *Homo sapiens* MX dynamin-like GTPase 2 (MX2), mRNA, (2015).
Database GenBank: NM_207315.3, *Homo sapiens* cytidine/uridine monophosphate kinase 2 (CMPK2) transcript variant 1, mRNA, (2016).

ANTIVIRAL PROTEINS AND THEIR USES IN THERAPEUTIC METHODS

CROSS-REFERENCE TO RELATED APPLICATIONS

This application is a 35 U.S.C. § 371 U.S. national entry of International Application PCT/US2017/019277, having an international filing date of Feb. 24, 2017, which claims the benefit of U.S. Provisional Application No. 62/299,086, filed Feb. 24, 2016, the content of each of the aforementioned applications is herein incorporated by reference in their entirety.

STATEMENT OF GOVERNMENTAL INTEREST

This invention was made with government support under grant no. R37DA013806 awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Feb. 23, 2017, is named P13969-02_SL.txt and is 37,018 bytes in size.

BACKGROUND OF THE INVENTION

Interferons are host defense cytokines that coordinate the expression of hundreds of cell-autonomous defense genes (interferon-stimulated genes; ISGs) to control viral infections in all vertebrates. Interferon-alpha 2b (IFN), a quintessential type 1 interferon, has been used to treat chronic viral infections including HIV. HIV infected individuals treated with IFN experience a decline in the abundance of plasma viral RNA5 and the number of cells harboring viral genomes, presumably by inducing ISGs that restrict HIV replication. For example, Sandler et al. recently demonstrated that inhibition of type-1 IFN signaling in rhesus macaques reduced ISG induction and enhanced SIV replication and progression to AIDS. Although type-1 interferons are critical for control of HIV, SIV, and other viral infections, the molecular mechanisms and even the cells in which ISGs that restrict HIV are induced are largely unknown.

SUMMARY OF THE INVENTION

One embodiment of the present invention is a method for preventing or treating HIV in a subject comprising administering to a subject an effective amount of a pharmaceutical composition comprising a synthetic protein selected from the group of BCL-G, CMPK2, LAMP3, functional parts thereof, recombinant proteins thereof, and combinations thereof. It is preferred that the synthetic protein is a human protein and not and animal protein and the synthetic protein is manufactured using a prokaryotic cellular or eukaryotic cellular in vitro system.

Another embodiment of the present invention is a method for preventing or treating HIV in a subject comprising administering to a subject an effective amount of pharmaceutical composition comprising a protein of Formula I $$P-G \qquad (I)$$

wherein P is a first protein selected from the group consisting of BCL-G, CMPK2, LAMP3, or functional parts thereof and G is a second protein such as a receptor binding domain. The first protein may be BCL-G, CMPK2 or LAMP3 or a functional part thereof.

Another embodiment of the present invention is a method for preventing or treating HIV in a subject comprising administering to a subject an effective amount of a pharmaceutical composition comprising a synthetic non-coding nucleic acid sequence of a gene selected from the group consisting of BCL-G, CMPK2, LAMP3, or a combination thereof, wherein the non-coding nucleic acid sequence restricts the expression of HIV in the subject. The preferred non-coding nucleic acid sequence is UC002qyO.4 (CMPK2 non-coding isoform) (SEQ ID NO: 1), UC002yzf.1 (MX2 non-coding isoform) (SEQ ID NO: 2), or a combination thereof. These non-coding nucleic acid sequences may be found on the UCSC Genome Browser developed and maintained by the Genome Bioinformatics Group, a cross-departmental team within the UC Santa Cruz Genomics Institute at the University of California Santa Cruz (UCSC).

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "activity" refers to the ability of a gene to perform its function such as Indoleamine 2,3-dioxygenase (an oxidoreductase) catalyzing the degradation of the essential amino acid tryptophan (trp) to N-formyl-kynurenine.

The term "antibody," as used in this disclosure, refers to an immunoglobulin or a fragment or a derivative thereof, and encompasses any polypeptide comprising an antigen-binding site, regardless of whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')$_2$, Fv, scFv, Fd, dAb, and other antibody fragments that retain antigen-binding function, i.e., the ability to bind, for example, PD-L1, specifically. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant." An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

Binding fragments of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')2 fragment in which the two arms of the antibody molecule remain linked and comprise two-antigen binding sites. The F(ab')2 fragment has the ability to crosslink antigen. "Fv" when used herein refers to the minimum fragment of an antibody that retains both antigen-recognition and antigen-binding sites. "Fab" when used herein refers to a fragment of an antibody that comprises the constant domain of the light chain and the CHI domain of the heavy chain.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "disease" is meant any condition or disorder that damages or interferes with the normal function of a cell, tissue, or organ. Examples of diseases include cancer.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "express" refers to the ability of a gene to express the gene product including for example its corresponding mRNA or protein sequence (s).

The term "fragment" refers to a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The term "functional part thereof" means a part of a protein or non-coding sequence that allows it to perform its function or activity, such as restricting the expression of HIV.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

By "reduces" or "restricts" is meant a negative alteration of at least 10%, 25%, 50%, 75%, or 100%.

A "reference" refers to a standard or control conditions such as a sample (human cells) or a subject that is a free, or substantially free, of an agent such as a composition of the present invention including one or more nucleic acids and/or protein sequences of BCL-G, CMPK2 or LAMP3.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

BRIEF DESCRIPTION OF THE DRAWINGS

FIGS. 4a to 4f illustrates interferon induces multiple isoforms of CMPK2 that differentially restrict HIV in vivo. (a) Genomic position of CMK2 and RSAD2, magnified on CMPK2, to show all UCSC annotated CMPK2 isoform exons that were detected. Detected variants that are Refseq annotated are shown in dark blue and non-Refseq UCSC annotated variants are shown in light blue. Arrow-studded lines indicate 5' to 3' directionality of transcripts and connectivity between exons (filled bars). Increased girth of bars indicates coding regions. (b) Sashimi plots showing the mapped read density [range] within regions of CMPK2 immediately before (Pre-IFN, blue), and 24 hours after the administration of IFN (Post-IFN, red). Curved lines are labeled with the number of reads spanning the indicated exon-exon junction. (c) Modified boxplots with points overlaid of post-correction fold-changes in each isoform with IFN treatment for each individual in which the measurement was possible. * P<0.01, **P≤0.0001. (d) Scatterplots showing the post-correction fold-change values for each gene with IFN and plasma HIV RNA decline. (e) Real-time qPCR data showing the up-regulation of individual isoforms for CMPK2, BCL-G, LAMP3, and MX2 in response to IFN in six cell lines at 0, 6, 12, and 24 hours. (f) Real-time qPCR data of CMK2, LAMP3, BCL-G, and MX2 in response to IFN in activated CD4+ T cells ex vivo from two healthy donors who were not infected with HIV or HCV.

DETAILED DESCRIPTION OF THE INVENTION

Figure 1:
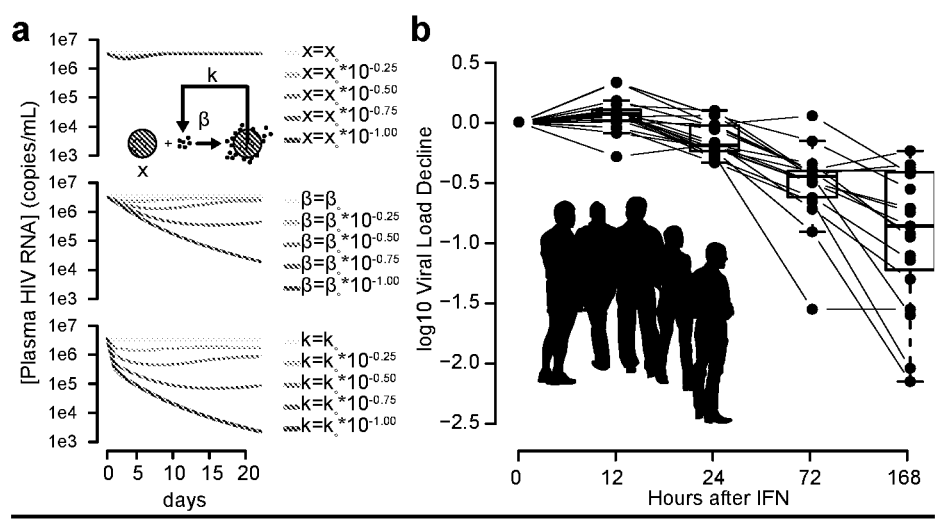
FIGS. 1a and 1b illustrates HIV kinetics are sensitive to changes in the rate of infection and the rate of virus production by IFN treatment in silico and in vivo. (a) Infections were first simulated for 1,000 days using three standard differential equations $dx/dt=\lambda-dx-\beta xv$, $dy/dt=\beta xv-ay$, and $dv/dt=ky-uv$ ($\lambda$=production rate of uninfected cells, x=number of uninfected cells, d=decay rate of uninfected cells, $\beta$=first order rate constant of infection, v=plasma viral load, y=number of infected cells, a=decay rate of infected cells, and k=first order rate constant of virus production in infected cells) using the starting values ($x=10^6$, $y=1$, $v=10^5$, $\lambda=10^5$, $d=0.1$, $a=0.5$, $B=2\times10^{-7}$, $k=100$, $u=5$). Resulting values were then used as input into the same equations, separately modifying the indicated variable by the indicated factor and run for 21 days. Varying $\beta$ and k had significant effects on HIV kinetics, whereas varying x had minimal effects. (b) Observed HIV kinetics after IFN in 19 participants. Boxplots with overlaid values of in vivo $\log_{10}$ copies/mL changes in HIV RNA in patients receiving IFN from baseline are shown with lines connecting values from each subject over the indicated time-points. Lines indicate longitudinal measurements from the same individual.

As mentioned above, the present invention includes methods for preventing or treating HIV in a subject comprising administering to a subject an effective amount of a pharmaceutical composition comprising one or more proteins including BCL-G, CMPK2, and/or LAMP3. Examples of nucleic acid and protein sequences of these genes in different organisms including humans may be found on the National Center for Biotechnology Information (NCBI) database and includes: 1) BCL-G, Accession Nos. AAG59794.1 (SEQ ID NO: 3) and AAG59793.1 (SEQ ID NO: 4), 2) CMPK2, Accession Nos. AA144203.1 (SEQ ID NO: 5) and AA141803.1 (SEQ ID NO: 6), and 3) LAMP3, Accession Nos., AIC56215.1 (SEQ ID NO: 7), and AA151599.1 (SEQ ID NO: 8) as examples. Mathematical modeling of in vivo HIV kinetics after IFN administration was developed that suggested that ISGs reduced either cell susceptibility or virus release (FIG. 1). Since activated CD4+ T cells are believed to be the principal source of HIV, the inventors hypothesized that decreases in plasma HIV viremia after IFN were caused by ISG induction in activated CD4+ T cells. Moreover, the inventor's reasoned that the natural variability in the human HIV response to IFN would reveal the particular ISGs that restrict HIV infection in vivo.

Modeling Plasma HIV RNA Kinetics After IFN.

Standard mathematical models of HIV kinetics was adapted after antiviral treatment to consider an array of ISGs as putative antivirals, accounting for how IFN might affect HIV viremia. The inventors hypothesized that ISGs could either affect the first order rate constant of target cell infection (1) or the rate of virus production in infected cells (k) (FIG. 1a). An example of an ISG that might affect β is MX2, which inhibits HIV pre-integration, whereas an example of an ISG that affects k is BST2 (tetherin), which prevents virus release. Modeling revealed that HIV kinetics after IFN administration were consistent with an effect of β and/or k, confirming the approach used in the present invention to study intracellular ISGs that might restrict the HIV replicative lifecycle. In contrast, an effect on the number of cells (x) could not explain the results, which is notable since IFN is known to reduce the number of circulating CD4+ T cells.

Administration of a single weight-based injection of IFN to 19 untreated HIV and HCV co-infected persons resulted in a cohort-wide median (range) 0.85 (0.24 to 2.14) $\log_{10}$ copies/mL decline in plasma HIV RNA at one week (P=0.003) that corresponded to our modeling (FIG. 1b). HCV viral kinetics were performed in parallel over the same intervals (13). Strikingly, HIV and HCV viral kinetics were not correlated within individuals over one week, indicating that each virus was restricted by a distinct set of ISGs and/or differential expression in permissive cells and is consistent with similar observations in co-infected patients on longer durations of therapy. Thus, investigation of HCV was performed independently.

RNA Sequencing from Activated CD4+ T Cells Before and After IFN.

Figure 2:
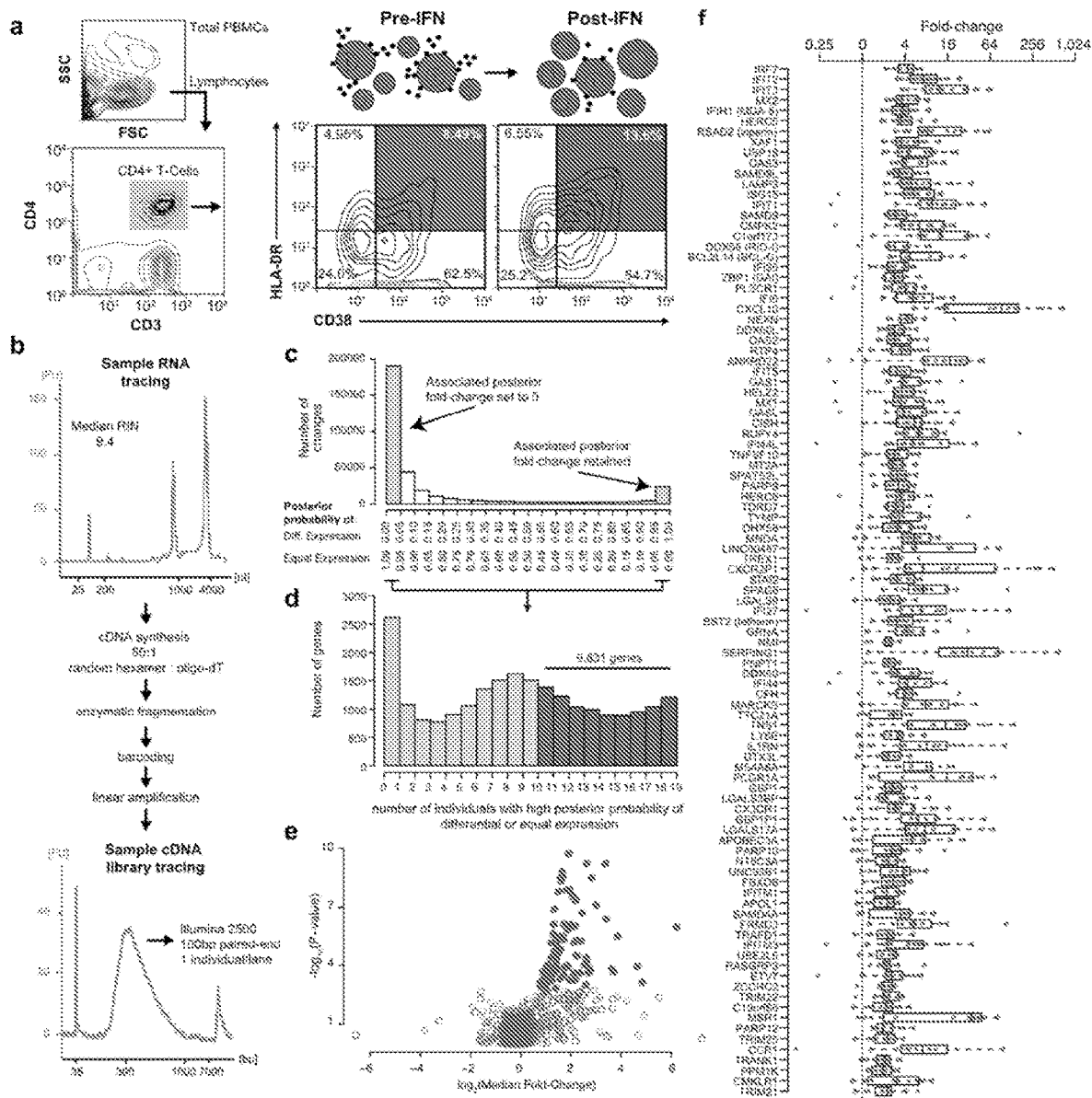
FIGS. 2a to 2f illustrate RNA sequencing of activated CD4+ T cells from HIV-infected persons before and after interferon administration reveals ISGs. (a) Flow cytometery data and sorting algorithm for isolation of activated CD4+ T cells from total PBMCs at baseline (Pre-IFN, blue) and after 24 hours after injection with IFN (Post-IFN, red). (b) Representative bioanalyzer tracing of RNA, overview of library preparation, and sample bioanalyzer tracing of prepared cDNA library. Fluorescence units, FU; RNA or cDNA length in nucleotides (nt). (c) Histogram showing the distribution of the posterior probability of differential vs. equal expression (PPDE and PPEE, respectively) for all genes in which a determination could be made over the two sampled time-points. Meta-data from a merged data set for all individuals is shown. (d) Histogram showing the distribution of the number of genes with the indicated number of individuals detecting that gene with PPDE or PPEE≥0.95. (e) Volcano plot comparing cohort-wide median post-correction fold-change values (with values corresponding to PPEE≥0.95 set to 0) and p-values for the 9,631 genes with high-confidence quantitation in at least 50% of the cohort (f) Boxplots with overlaid points showing the individual fold-changes for the 99 genes that significantly changed with IFN across the cohort after adjustment for multiple comparisons with no fold-change adjustment imposed for PPEE values 0.95.

Peripheral blood mononuclear cells (PBMCs) were collected before and 24 hours after IFN. Activated CD4+ and CD8+ T cells, defined by co-expression of CD38 and HLA-DR, were quantified before and after IFN by flow-cytometery (FIG. 2a). Compared to pre-IFN, the percent of CD4+/CD38+/HLA-DR+ and CD8+/CD38+/HLA-DR+ T cells increased by a median (IQR) 5.4 (−1.6 to 6.9; P=0.02) and 19.1 (14.2 to 22.5; P=0.0001), respectively, after IFN. HIV viremia is largely composed of virus released from activated CD4+ T cells; therefore, focus was placed on this population of cells to see if systemically administered IFN controlled viremia by inducing antiviral ISGs in activated CD4+ T cells. Activated CD4+ T cells pre- and post-IFN and RNA were sorted from these cells was sequenced (FIG. 2b) and analyzed for changes in gene and splice variant expression (FIG. 2c).

Defining an Empirical Set of ISGs in Activated CD4+ T Cells.

Since it was not known which genes would be induced by administration of IFN in activated CD4+ T cells in vivo, we first determined which genes were induced by IFN in the cohort. A Bayesian clustering model was employed to determine which genes were likely to be differentially expressed after IFN (FIG. 2c). In total, 21,930 genes were evaluable in at least one individual, and 9,631 were differentially expressed with a posterior probability ≤0.95 in ≤11 members of the cohort, which was the pre-determined threshold for further study (FIG. 2d). The resulting loge fold-changes after Bayesian correction for all individuals were tested and significance was adjusted for multiple comparisons (FIG. 2e). This yielded a de novo set of 99 genes that were bona fide ISGs in activated CD4+ T cells (FIG. 2f). These ISGs included multiple known HIV restriction factors such as MX2 and tetherin, which we predicted to be involved in constraining β and k, respectively, by our modeling. In addition, several ISGs with previously described activity against other viruses (RSAD2 [viperin], DDX58 [RIG-I], and IFITM3) were also identified, as were genes that have not been previously described as having antiviral roles (including but not limited to BCL-G [BCL2L14], CMPK2, and LAMP3).

An Algorithm for Identifying HIV Restriction Factors.

Figure 3:
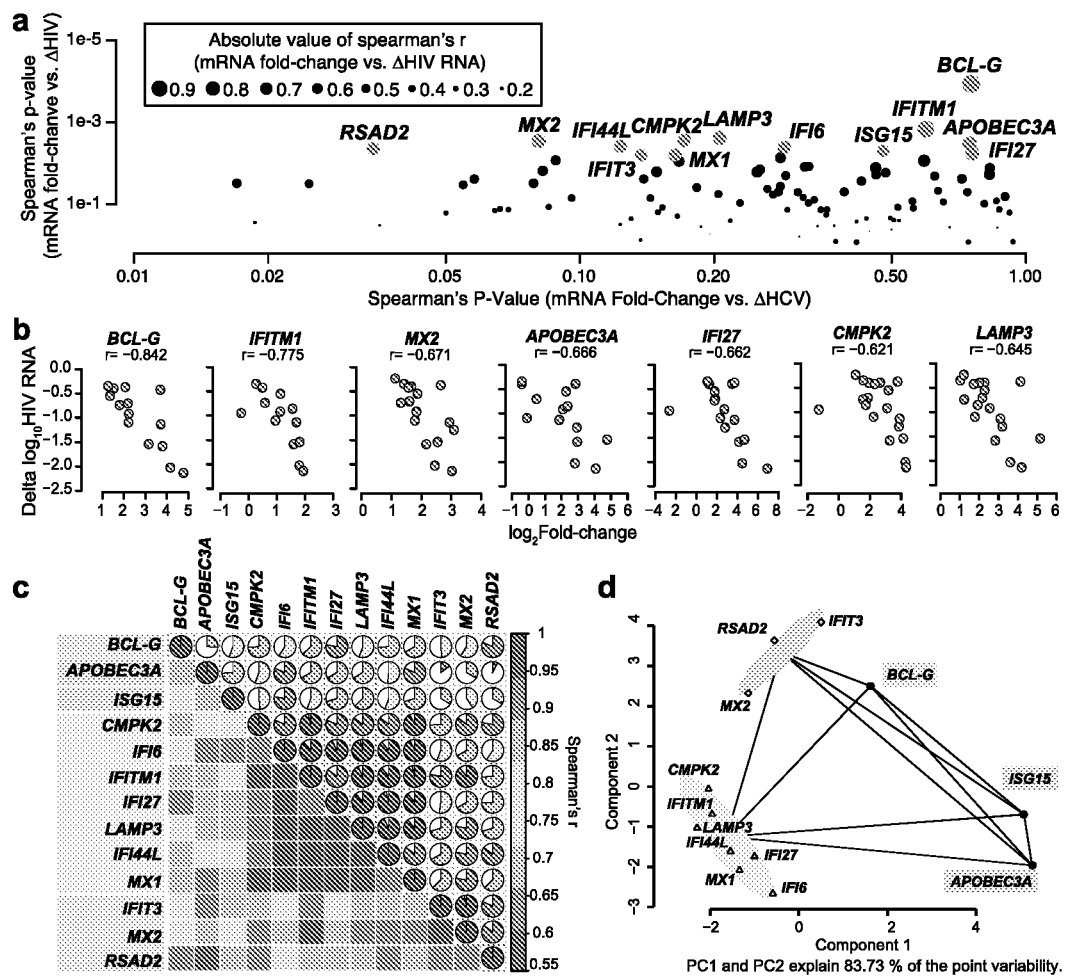
FIGS. 3a to 3d illustrates an integrated algorithm to determine putative interferon-induced HIV restriction factors in activated CD4+ T cells. (a) Spearman correlations were performed for the induction of each of 99 ISGs defined in FIG. 2 and the decline in plasma HIV viremia. Represented are the P-value (y-axis) and the correlation coefficient (size of each dot). Genes that met statistical significance after adjustment for multiple comparisons are shown as green dots. To validate against false detection, Spearman correlations were also performed for the induction of the same genes and plasma HCV viremia (P-values along the x-axis), revealing no genes that were upregulated in activated CD4+ T cells were significantly associated with HCV decline after adjustment for multiple comparisons. (b) Individual scatterplots of 7 genes that were significantly correlated to plasma HIV RNA decline after adjustment for multiple comparisons (c) Pairwise correlation plots of fold-changes for the putative HIV restriction factors. (d) K-means clustering of principal component analysis grouping all points into 5 clusters. The same color scheme used to demark clusters in (d) is used in (c).

As expected, there was person-to-person variability in both expression of potential restriction factors and HIV RNA decline (FIGS. 1b and 3a). To further identify which RNAs were responsible for the decline in plasma HIV viremia, an algorithm was developed that ranked candidates according to viral load decline. The algorithm revealed 13 genes whose upregulation in activated CD4+ T cells was closely correlated with plasma HIV RNA decline across the 19 individuals. Performing the same algorithm using HCV kinetics in the same people demonstrated that the induction of these ISGs were uniquely correlated with plasma HIV RNA decline (FIG. 3a). The 13 putative HIV restriction ISGs included MX2 and IF16, two genes that are known to restrict HIV in vitro. In addition, several genes were identified for which no evaluation of antiviral activity has been performed, including BCL-G, CMPK2, and LAMP3.

The inventors next asked whether these 13 putative restriction factors for HIV were induced by IFN in clusters, to test whether their effects on HIV were independent. Pairwise correlation analysis of post-correction fold-change values revealed a hierarchy in the relatedness of gene induction (FIG. 3c). k-means clustering was performed on principal component analysis of the fold-change values and resolved genes into five distinct clusters of genes with BCL-G, APOBEC3A, and ISG15 each in their own cluster and the rest of the genes contained in two additional clusters (FIG. 3d). Interestingly, RSAD2 and CMPK2 are directly adjacent to each other on chromosome 2 (FIG. 4a), yet they segregated into two distinct clusters with other members distributed across different chromosomes, suggesting that the CMPK2 locus is differentially regulated from the RSAD2 locus.

Specific ISG Isoforms are Associated with HIV Restriction.

Genes were subsetted by their transcriptional variants for MX2, CMPK2, and BCL-G to test the hypothesis that individual isoforms were responsible for HIV restriction (LAMP3 has only one annotated variant). Five distinct transcript variants of MX2 were examined for their induction by IFN and their relationship with viral restriction. Four out of the five (3 coding and 1 non-coding) variants were significantly induced by IFN ($P<0.05$ for all). Only one of the three coding variants (uc002yzf.1 (SEQ ID NO: 2)), also known as the full-length MX2, was both induced and associated with HIV restriction ($P=0.02$). In addition, the non-coding variant of MX2, which contains the first exon and a partially-spliced retained intron (uc002yzf.1 (SEQ ID NO: 1)), was highly expressed and associated with both HIV restriction ($P=0.023$) and full-length MX2 expression ($P=3.4\times10^{-7}$), although their splicing is mutually exclusive.

Figure 4:
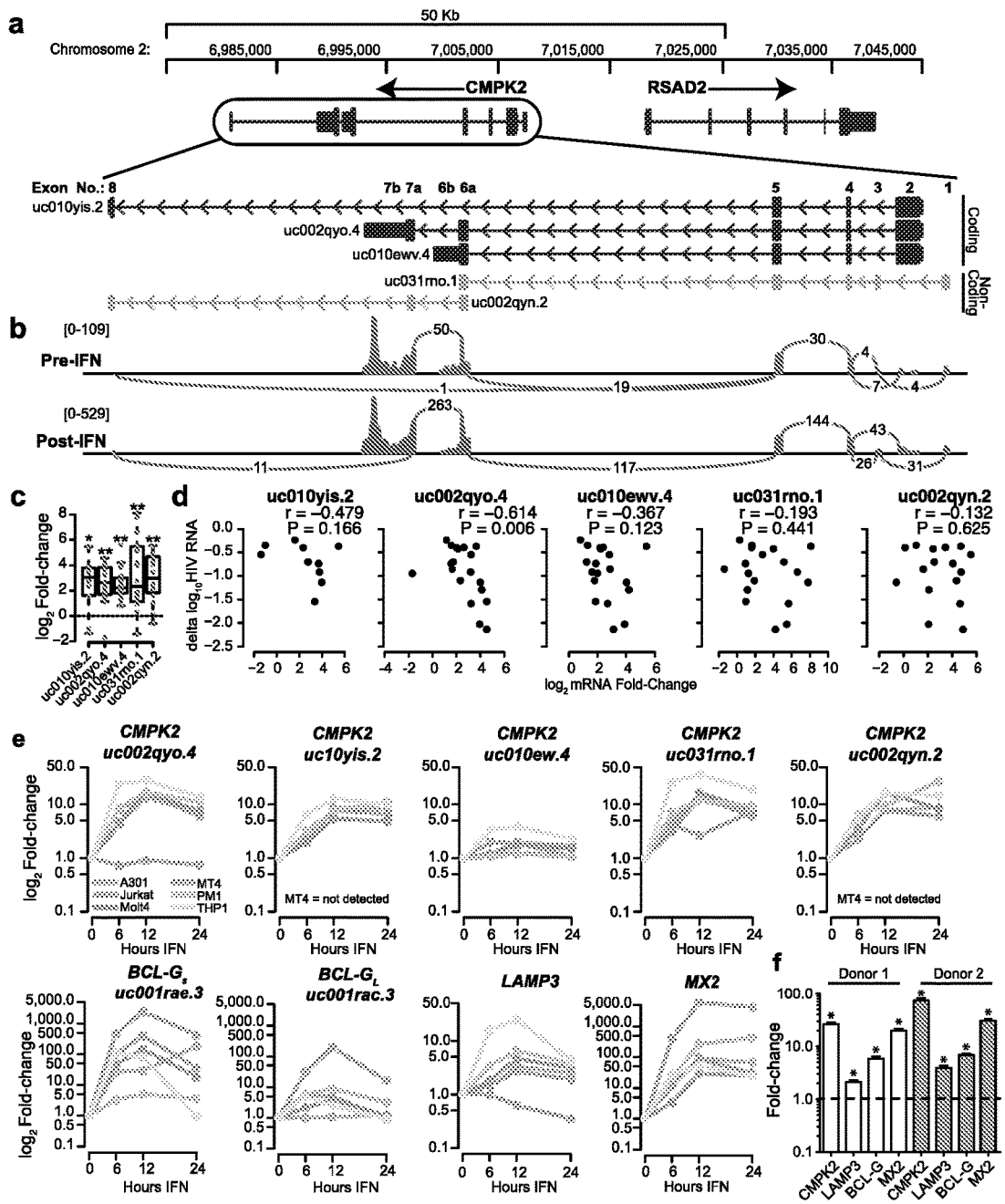
FIG. 4 discloses "uc010yis.2" as SEQ ID NO: 11, "uc002qyo.4" as SEQ ID NO: 1, "uc010ewv.4" as SEQ ID NO: 12, "uc031rno.1" as SEQ ID NO: 13 and "uc002qyn.2" as SEQ ID NO: 14.

Examination of CMPK2 spliceoforms revealed a significant increase in the expression of all five detected isoforms (3 coding and 2 noncoding; FIGS. 4a and 4b) after IFN ($P<0.05$ for each; FIG. 4c). However, similar to MX2, only one coding variant (uc002qyo.4 (SEQ ID NO: 1)) was associated with a decline in plasma HIV RNA level after IFN ($P=0.006$; FIG. 4d). Although all three BCL-G isoforms were induced by IFN, no single isoform was associated with plasma HIV RNA decline.

CMPK2, BCL-G, and LAMP3 are Induced by IFN In Vitro and Ex Vivo in the Absence of HIV Infection.

The inventors confirmed that IFN induced the putative HIV restriction factors BCL-G, LAMP3, and CMPK2 in multiple cell lines and over a 24 hour time course by quantifying intracellular mRNA levels of each gene using RT/qPCR with qPCR primer sets spanning unique exons or exon/exon junctions to distinguish the individual isoforms-(FIG. 4e). All three putative restriction factors were upregulated upon IFN treatment in most of the cell lines that were tested, although to different degrees. Notably, some isoforms of each gene were more robustly induced than others: e.g., BCL-GL isoform uc001rac.3 (SEQ ID NO: 9) exhibited <10-fold IFN-induction in 5/6 cell lines, whereas BCL-Gs isoform uc001rae.3 (SEQ ID NO: 10) exhibited >10-fold induction in 5/6 cell lines. CMPK2 isoform uc002qyo.4 (SEQ ID NO: 1) was induced in 5/6 cell lines, although not in MT4 cells (FIG. 4e). Additionally, CD4+ T cells were activated ex vivo from two donors not infected with HIV or HCV and stimulated with IFN for 24 hours. The major isoforms of CMPK2, LAMP3, BCL-G, and MX2 were similarly up regulated in both individuals (FIG. 4f).

IFN-Mediated Restriction of HIV Depends on CMPK2 and BCL-G.

Figure 5:
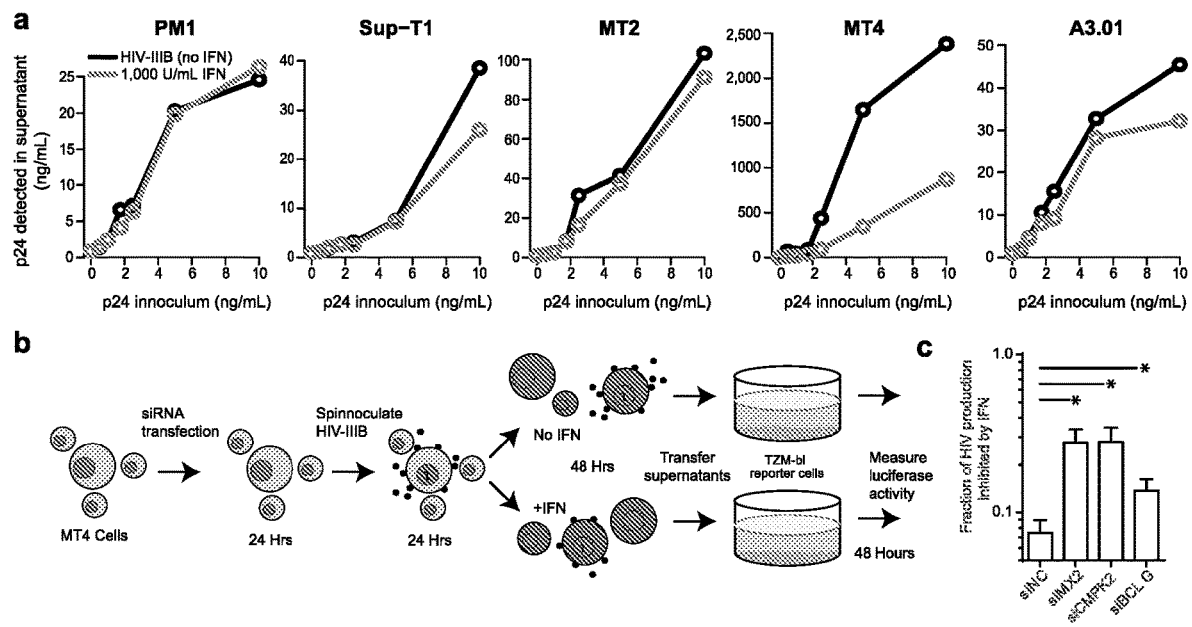
FIGS. 5a to 5c illustrates interferon-induced HIV restriction in vitro is dependent on CMPK2 and BCL-G. (a) Production of HIV (y-axis) in different cell lines that were inoculated with varying concentrations of HIV-IIIB (x-axis). One day after infection, cells were either left untreated (black) or treated with 1,000 U/mL IFN (red) and incubated for 72 hours. HIV p24 was measured in supernatants after 72 hours. (b) Experimental scheme for measuring IFN-mediated inhibition of HIV in cells in which CMPK2 and BCL-G have been knocked down by RNAi. (c) Barplots showing fraction of HIV production, as measured by the TZM-bl luciferase assay, compared to untreated cells. Error bars indicated standard error over the mean from 3 replicate transfections. * indicates P<0.05.

Cell line(s) supported robust HIV replication that was inhibited by IFN were identified. Six cell lines were inoculated with infectious HIV at titrated concentrations to develop growth curves of replicating virus (FIG. 5a). Inoculated cultures were split into two wells, one remaining untreated and the other treated with IFN to inhibit viral replication. MT4 cells appeared to support the most robust HIV replication and were also the most susceptible to the antiviral effect of IFN.

RNAi was used to determine if CMPK2 and BCL-G expression contributed to IFN-mediated restriction of HIV in vitro. MT4 cells were transfected with siRNAs directed against CMPK2, BCL-G, and MX2 as a positive control and then treated cells with IFN (FIG. 5b). IFN resulted in a 92.6%±1.5% inhibition of virus production in cells transfected with negative control siRNAs (FIG. 5c). As expected, siRNA against MX2 (siMX2) attenuated IFN inhibition of HIV production resulting in a 73.3%±6.0% replication inhibition ($P=0.015$; FIG. 5c). Similarly, siRNAs against CMPK2 (siCMP2) attenuated IFN inhibition resulting in a 73.5%±6.6% replication inhibition ($P=0.019$; FIG. 5c).

siRNA against BCLG (siBCLG) attenuated IFN inhibition resulting in a 86.3%±2.5% replication inhibition (P=0.049; FIG. 5c).

By sequencing mRNAs in the principal cells in which HIV replicates and investigating differences in the induction of those RNAs against differences in the reduction of plasma HIV RNA, CMPK2 and BCL-G were identified as two novel IFN-induced HIV restriction factors. We also show, for the first time, that IFN induces MX2 in vivo to restrict HIV viremia. The findings of the present invention underscore the remarkable diversity of the IFN transcriptional program and provide unique insights into which of the multiple ISGs have direct antiviral (beneficial) roles. Accordingly, the results suggest new approaches to the control of chronic HIV infection by administering to a subject with HIV a pharmaceutical composition of one or more specific ISG proteins or non-coding isoforms including BCL-G, CMPK2, LAMP3 that restrict the transcriptional expression of HIV.

Differences have been shown in the transcriptional program of a cell type impact its susceptibility to HIV and its IFN sensitivity. To the best of the inventor's knowledge, this is the first study that has focused on discovery of novel HIV restriction factors in activated CD4+ T cells from infected persons. In addition, by using an open-ended sequencing approach, the inventors were able to develop a rigorously-defined panel of ISGs in activated CD4+ T cells, expanding the list of ISGs that have been previously described as relevant in HIV.

CMPK2 has been annotated as an ISG before, but its antiviral activity has been unclear. Its genomic location on chromosome 2 is nestled between RSAD2 and the newly described Negative Regulator of the Interferon Response (NRIR), an interferon-induced long non-coding RNA that is a negative regulator of IFN responses. Hence, CMPK2 sits in a transcriptionally active hotspot for IFN regulation. Notably, our data collectively support that CMPK2, and not RSAD2 or NRIR, restricts HIV replication. CMPK2 catalyzes the phosphorylation of dUMP to dUDP, an intermediate step in the overall conversion of dUMP to dUTP. Uracylation of retroviral genomes has been recently reported to be a novel mechanism of HIV restriction, although it is not clear that this process involves CMPK2. All CMPK2 coding isoforms contain the active site of the translated protein, and all were induced by IFN, so it is not clear why only the uc002.qyo.4 isoform (SEQ ID NO: 1) was associated with HIV restriction in vivo. The CMPK2-uc002.qyo.4 isoform (SEQ ID NO: 1) differs from the other isoforms only in an additional 41 amino acids at the N-terminus, and in that it has a unique 3'UTR. These differences suggest that the CMPK2-uc002.qyo.4 (SEQ ID NO: 1) isoform may possess modified activity conferred by the additional domain and/or that the stability of its transcript is improved by usage of this 3' UTR.

The function of BCL-G remains poorly understood. There is controversy as to whether BCL-G is involved in apoptosis. Its nomenclature derives from its BH2 and BH3 domains, although the extent of its similarity to canonical BH-containing proteins such as BCL2 is unknown. While knockdown of BCL-G isoforms significantly limited IFN-mediated HIV restriction, it was to a lower extent than CMPK2 or MX2. This may have been due to the observation that MT4 cells, the cell type in which the RNAi experiment was performed, was the most potent inducer of BCL-G and significant residual induction through IFN treatment still occurred. More potent suppression or oblation of the locus is needed to confirm this hypothesis.

Several challenges were encountered in this investigation. Biases in reverse transcription and the library preparation may have favored the most abundant transcripts that were then targeted for sequencing, omitting less abundant but still relevant transcripts. This may have resulted in patchy quantification of some transcripts across the cohort. To account for this possibility, the inventors only analyzed transcripts that were detectable in ≥11/19 individuals to ensure that only consistently detected genes were considered. While this limitation may have excluded genes that play a role, it would not limit our confidence in the two novel factors identified. A second challenge was in selecting CD4+ T cell markers that corresponded well with HIV infected or HIV susceptible cells. CD38 and HLA-DR, well-established markers of activated CD4+ T cells, were used although it is possible that other markers would have more specifically identified HIV susceptible cells. Focusing on only HIV infected cells, however, would have omitted the effects of IFN on preventing infection of new cells, which translates mathematically to which ISGs impact $\beta$, the first order rate constant of infection (FIG. 1). An important point is that there may not have been sufficient power to do a complete isoform analysis on all of the 21,930 unique genes that were sequenced. Instead, the present invention focused on isoforms of individual genes of interest after employing the computational algorithm to identify HIV restriction factors. Further research is needed to fully understand how the functional activities of these isoforms differ, especially with regard to CMPK2 and MX2. Furthermore, while the in vitro RNAi experiments against CMPK2 demonstrated that it plays a role in IFN-mediated HIV restriction, this was evident in the MT4 cell line, which did not demonstrate a substantial increase in CMPK2 expression upon IFN stimulation. This result, however, still suggests that CMPK2 catalysis is rate-limiting for IFN-mediated restriction of HIV. Finally, studies were performed on interferon alpha 2b. It is possible and even likely that other type 1 interferons could have induced a distinct set of genes that restricted HIV by other mechanisms. However, that consideration does not detract from our confidence in revealing the mechanism through which interferon alpha, the most common therapeutic interferon, constrains HIV.

The present invention provide evidence for three novel interferon-induced HIV restriction factors, BCL-G, CMPK2, LAMP3. HIV restriction factors provide insights into the ongoing battle between pathogen and host, and may provide novel therapeutic targets for HIV control. The genes we identified are highly variable in their induction from host-to-host, providing an inconsistent landscape of restriction for HIV to realize fitness advantage through resistance. Whether or not this is a protective mechanism for host species whose generation time and mutation rates are miniscule in comparison to viruses remains to be determined.

EXAMPLES/METHODS

Modeling the Contributions of Various Features of HIV Infection.

The three differential equations $dx/dt=\lambda-dx-\beta xv$, $dy/dt=\beta xv-ay$, and $dv/dt=ky-uv$ ($\lambda$=production rate of uninfected cells, x=number of uninfected cells, d=decay rate of uninfected cells, $\beta$=first order rate constant of infection, v=plasma viral load, y=number of infected cells, a=decay rate of infected cells, and k=first order rate constant of virus production in infected cells) were integrated using "integrateODE" function in the 'mosiac' package version 0.9.2-2 in R (www.r-project.org) version 3.1.2 for 1000 days using standard starting values (x=1e6, y=1, v=100000, λ=1e5, d=0.1, a=0.5, B=2e-7, k=100, u=5). The solution values were then used as input into another integration but varying either x, β k, or a by the indicated factor and run to simulate an additional 3 weeks (300 days for a) with these new imposed values.

Human Subjects.

The primary outcome of the study was to compare gene expression in activated CD4+ T cells with HIV RNA changes in plasma following administration of IFN ($\Delta HIV_{IFN}$): 20 persons with HIV-HCV co-infection were enrolled in a prospective study of HIV and HCV viral kinetics pre-antiretroviral therapy (ART). Persons with chronic HIV and HCV infections were recruited from the Johns Hopkins HIV Clinic, the Baltimore City Sexually Transmitted Diseases Clinic, and other area clinics. HIV infection was established by detection of HIV antibodies and an HIV RNA level >400 c/mL; chronic HCV infection was determined by detection of HCV antibodies and HCV RNA >100,000 IU/mL for >6 months. Subjects had received <24 months of ART over their entire lives and none within 6 months. Subjects also were excluded if HBsAg was detected in plasma; they were pregnant; there was a history of severe depression or any uncontrolled disease; platelet count was <50,000/mm$^3$; there was a contraindication to use of raltegravir, tenofovir DF, or emtricitabine. Because therapy was judged too urgent to wait for study procedures as per current treatment guidelines for HIV and HCV, persons at screening whose CD4+ T lymphocyte counts were <200/mm$^3$ or who had cirrhosis were excluded. A total of 32 patients were screened to identify 20 study subjects. All subjects gave written informed consent to the protocol as approved by the Johns Hopkins Institutional Review Board.

Subjects were admitted to the Johns Hopkins Hospital Clinical Research Unit. A single 1.5 μg/kg of peginterferon alpha 2b (IFN) was administered subcutaneously. Thereafter, blood was collected every 6 hours and the patient was discharged 24 hours after the IFN dose. The patient returned 48 hours, 72 hours, 7 days, and 14 days after the IFN dose. The Johns Hopkins University School of Medicine Institutional Review Board approved this study.

Laboratory Testing.

Unless otherwise indicated, all laboratory testing was performed in the clinical laboratory of the Johns Hopkins Hospital.

Viral RNA Testing. To reduce interassay variance, HCV and HIV RNA testing for a given subject was done at the same time on plasma centrifuged within 30 minutes of collection and stored at −20° C. for up to 25 hours and then at −80° C. until testing. HIV RNA testing was done using the Abbott RealTime HIV Assay (No. 02631-090). HCV RNA testing was done using the Abbott RealTime HCV Amplification Reagent Kit (No. 04J86-90, Des Plaines, Ill.). To provide information in "real time," such as for screening into the study, additional HCV RNA tests were done by the commercial laboratory of the Johns Hopkins Hospital using the Roche Cobas AmpliPrep/Cobas TaqMan HCV Test, v. 1.0. Although both were reported in international units, analyses were primarily done on results from one or the other laboratory. CD4+ T cell count was measured by flow cytometry of whole blood that was delivered to the Johns Hopkins Hospital clinical laboratory.

Isolation of Activated CD4+ T Cells.

Peripheral blood mononuclear cells (PBMCs) were separated from whole blood and frozen as previously described. Freshly thawed cells were washed and incubated with CD3-FITC (Biolegend), CD4-PECy7 (Biolegend), CD8-APC (BD Biosciences), HLA-DR-PE (Biolegend), and CD38-BV421 (Biolegend) for 40 minutes at 4° C. per the manufacturer's recommendation. Immediately before sorting, plasma membrane compromised cells were labeled with propidium iodide (Sigma). Flourescence-activated cell sorting (FACS) was performed on a MoFlo Legacy Sorter (Beckman-Coulter) at the Johns Hopkins School of Public Health Flow Cytometery Core Facility. The population of interest was sorted directly into volumes of Quick-RNA® MicroPrep lysis buffer (Zymo Research) per the manufacturer's recommendation. Sorting was stopped when the number of sorted cells reached 125,000 cells although many samples did not reach this number. Flow-cytometry analysis on two randomly selected post-sort samples revealed >95% purity. Sorted samples were vortexed, incubated for 10 minutes at room temperature, vortexed again, and frozen at −80° C. until isolation.

Activated CD4+ T Cell RNA Isolation.

Isolation was performed using the Quick-RNA® MicroPrep kit (Zymo Research) according the manufacturer's protocol without the on-column DNAase treatment. The eluate was treated with DNAse-I (Qiagen) according to the manufacturer's protocol then purified and concentrated using the RNA Clean-up and Concentrator kit (Zymo Research) according the manufacturer. The high-sensitivity assay for RNA or DNA was performed on RNA isolations and cDNA libraries respectively using a 2100 Biolanalyzer (Agilent).

Library Preparation and Sequencing.

Complementary DNA (cDNA) libraries were produced using the Ovation® Single-cell RNAseq kit (NuGEN) according to the manufacturer's specifications. Briefly, reverse transcription was carried out using a random hexamer to oligo-dT ratio of 50:1 and unique barcodes for each individual's samples were ligated to ~250 bp enzymatically fragmented molecules. All samples were linearly amplified with 19 cycles of PCR using primer annealing sites contained within the adapters. All sequencing was performed on a HiSeq2500 (Illumina) at the Johns Hopkins Genetics Research Core Facility.

Sequence Mapping and Differential Expression Calculation.

Reads were aligned to the hg19 reference genome and annotated transcripts with RSEM (version 1.2.9). Differential expression of genes and isoforms was calculated using EBseq (version 1.11.0), an empirical Bayes hierarchical model for expression analysis of RNAseq data. All sequence mapping and differential expression calculation was performed at the Johns Hopkins University Sidney Kimmel Comprehensive Cancer Center Next Generation Sequencing core.

Statistical Analyses.

Comparison values, including post-correction fold-change, post-correction probability of differential expression (PPDE), and post-correction probability of equal expression (PPEE) values, were further analyzed in using 'stats' in R version 3.1.2. Measurements for which neither the PPDE nor PPEE were 0.95 were discarded. In the determination of significance of the gene's change across the cohort, all fold-change calculations with PPEE 0.95 were set to 0. If there were remaining measurements for a gene in >10 of the individuals, a two-sided one-sample T-test was performed on loge transformed fold-change values. The resulting P-values were adjusted for multiple comparisons using the Benjamin-Hochberg method.[31] Genes with adjusted P-values 0.05 were considered ISGs. Spearman rank-correlations were performed between fold-changes between the observed ISGs and viral load decline with fold-changes with PPEE 0.95 retained as their original values. Pairwise correlation plots were constructed using torrplot (version 0.73). K-means clustering was performed using 'cluster' version 1.15.3. Wilcoxon rank-sum tests were performed on untransformed data in discovery analyses unless indicated otherwise. Two-sample unpaired one-way t-tests were performed in cell-culture studies as these experiments were performed to validate observations previously made in vivo.

In Vitro IFN Treatments.

Six cell lines THP-1, MT4, MOLT4, A3.01, PM1, and Jurkat cells (NIH AIDS Reagent Bank) were treated with 1,000 U/mL IFN for 0, 6, 12, and 24 hours and RNA was isolated using the QuickRNA microprep kit (Zymo Research). Reverse transcription was performed using SuperScript III (Invitrogen) according to the manufacturer's protocol using oligo-dT primers only. Quantitative PCR was performed using LightCycler SybrGreen master mix (Bio-Rad) according to the manufacturer and run on the Light-Cycler 480 (BioRad) according to the manufacturer's protocol (Primer sequences in Supplemental Table 2). Fold-changes are shown in reference to untreated samples and normalized to the geometric mean of Ct values from RPL13A (Integrated DNA technologies Assay ID: Hs.PT.58.47294843), RPL37 (Integrated DNA technologies Assay ID: Hs.PT.58.20168410), and β-actin (Integrated DNA technologies Assay ID: Hs. PT.56a.40703009. g).

Ex Vivo IFN Treatments.

PBMCs from two healthy platelet donors from the Johns Hopkins Transfusion Center were isolated and frozen as previously described. Thawed cells were cultured in 10% FBS RPMI containing 1.6 ng/mL IL-2 and 1 µg/mL phytohaemagglutinin for three days after which CD4+ T cells were magnetically separated using an antibody-based negative selection CD4+ T cell separation kit (Miltenyi). For each donor, duplicate 24-hour treatments with 0 or 1,000 U/mL IFN were performed. To adjust for differences in cell growth, the same number of counted cells was isolated from each condition using the RNeasy Plus RNA isolation kit (Qiagen) according to the manufacturer's protocol. Reverse transcription was performed using SuperScript III (Invitrogen) according to the manufacturer's protocol. Quantitative PCR was performed using LightCycler SybrGreen master mix (BioRad) according to the manufacturer and run on the LightCycler 480 (BioRad) according to the manufacturer's protocol (Primer sequences. Primers for uc002qyo.4 (SEQ ID NO: 1) were used for CMPK2 and primers for uc001rac.3 (SEQ ID NO: 9) were used for BCL-G. Fold-changes are shown in reference to samples treated with 0 U/mL IFN and normalized to the geometric mean of Ct values from RPL13A (Integrated DNA technologies Assay ID: Hs.PT.58.47294843), RPLPO (Integrated DNA technologies Assay ID: Hs.PT.58.20222060), and HPRT1 (Integrated DNA technologies Assay ID: Hs.PT.58v.45621572).

Virus Preparation.

The full-length HIV-IIIB, pNL4.3 delta nef GFP or pNL4.3 delta env (mock) plasmids were transfected into 293T cells and supernatants were spinnoculated onto PM1 cells (NIH AIDS Reagent Bank) for 2 hours at 1,200 g. Cells were then incubated at 37° C. for 10 days. Supernatants were passed through 0.22 µm filter and virus was pelleted through a 20% sucrose layer for 2 hours at 150,000 g. Pellets were resuspended in RPMI containing 10% FBS and stored at −80° C. Virus concentration was determined using the 96-well format Alliance HIV P24 Antigen Elisa kit (Perkin-Elmer, Waltham, Mass.) according to the manufacturer's protocol.

Testing Cell Lines for their IFN-Mediated Restriction Potential for HIV.

The indicated five cell lines (NIH AIDS Reagent Bank) were centrifuge inoculated with varying amounts of HIV-IIIB. For each inoculum concentration, 200,000 cells were centrifuge inoculated with 50 µL of RPMI containing 10% FBS at 1,200 g for 2 hours. Cells were allowed to rest for 24 hours at 37° C. and then each inoculum was split into two wells, one that received no treatment while the other received 1,000 U/mL IFN. Both wells were incubated for an additional 72 hours at 37° C. before supernatants were collected and p24 measurements were performed.

In Vitro RNAi, Infection, IFN Treatment, and Measurement of HIV Production.

MT4 cells (NIH AIDS Reagent Bank) were transfected with SMARTpool siGENOME siRNAs (Dharmacon) negative controls or siRNAs at 100 nM against the indicated gene of interest using the Amaxa Cell Line Nucleofector V kit (Lonza, Basel, Switzerland) according to the manufacturer's protocol. Cells were rested in recovery media (20% FBS) at 37° C. for 24 hours and 200,000 cells were centrifuge-innoculated with purified replication-competent HIV-IIIB (10 pg p24) in 50 uL 10% FBS RPMI at 1,200 g for 2 hours. After washing twice with media, cells were rested for 24 hours at 37° C. and split into two wells: one containing 1,000 Units IFN/mL and one containing an equal volume of the same 10% FBS RPMI used to resuspend the IFN (untreated). After 48 hours of IFN treatment, supernatants were removed, diluted 1:1,000 in DMEM containing 10% FBS. One hundred microliters of this dilution was transferred to 10,000 TZM-bl cells (NIH AIDS Reagent Bank) in 100 uL DMEM containing 10% FBS and 20 µg/mL DEAE and incubated at 37° C. for 48 hours. Cells were washed with PBS and assayed for luciferase activity using the Luciferase assay kit (Promega, Madison, Wis.). Fraction infection was calculated by dividing the luciferase reading from the IFN-treated wells by the luciferase reading from the untreated cells.

All references, including publications, patent applications, and patents, cited herein are hereby incorporated by reference to the same extent as if each reference were individually and specifically indicated to be incorporated by reference and were set forth in its entirety herein.

Embodiments of the disclosure concern methods and/or compositions for treating and/or preventing HIV in subjects including a pharmaceutical composition comprising a synthetic protein selected from the group of BCL-G, CMPK2, LAMP3, functional parts thereof, recombinant proteins thereof, and combinations thereof or a pharmaceutical composition comprising a synthetic non-coding nucleic acid sequence of a gene selected from the group consisting of BCL-G, CMPK2, LAMP3, or a combination thereof (the pharmaceutical compositions of the present invention).

In certain embodiments, the level to which HIV expression is restricted. The level of HIV expression may decrease by at least 2, 3, 4, 5, 10, 25, 50, 100, 1000, or more fold expression compared to the level of expression in a standard (such as an HIV positive subject without being administered one or more pharmaceutical compositions of the present invention), in at least some cases. An individual may monitor expression levels of HIV using standard methods in the art, such as northern assays or quantitative PCR, for example.

An individual known to have HIV, suspected of having HIV, or at risk for having HIV may be provided an effective amount of one or more pharmaceutical compositions of the present invention. Those at risk for HIV may be those individuals having one or more genetic factors, may be of advancing age, and/or may be immunocompromised, for example.

In particular embodiments of the disclosure, an individual is given an agent for HIV therapy in addition to the one or more pharmaceutical compositions of the present invention. Such additional therapy may include other HIV drugs, for example. When combination therapy is employed with one or more pharmaceutical compositions of the present invention, the additional therapy may be given prior to, at the same time as, and/or subsequent to the one or more pharmaceutical compositions of the present invention.

Pharmaceutical Preparations

Pharmaceutical compositions of the present invention comprise an effective amount of one or more nucleic acids and/or protein sequences of BCL-G, CMPK2 or LAMP3, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one or more nucleic acids and/or protein sequences of BCL-G, CMPK2 or LAMP3 or additional active ingredient will be known to those of skill in the art in light of the present disclosure, as exemplified by Remington: The Science and Practice of Pharmacy, $21^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The pharmaceutical compositions of one or more nucleic acids and/or protein sequences of BCL-G, CMPK2 or LAMP3 may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The pharmaceutical composition including one or more nucleic acids and/or protein sequences of BCL-G, CMPK2 or LAMP3 may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include one or more nucleic acids and/or protein sequences of BCL-G, CMPK2 or LAMP3, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the one or more nucleic acids and/or protein sequences of BCL-G, CMPK2 or LAMP3 may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In one embodiment of the present disclosure, the one or more nucleic acids and/or protein sequences of BCL-G, CMPK2 or LAMP3 are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, one or more nucleic acids and/or protein sequences of BCL-G, CMPK2 or LAMP3 may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the active compound or one or more nucleic acids and/or protein sequences of BCL-G, CMPK2 or LAMP3 may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, one or more nucleic acids and/or protein sequences of BCL-G, CMPK2 or LAMP3 may be comprised in a kit.

The kits may comprise a suitably aliquoted one or more nucleic acids and/or protein sequences of BCL-G, CMPK2 or LAMP3 and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the one or more nucleic acids and/or protein sequences of BCL-G, CMPK2 or LAMP3 and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The one or more nucleic acids and/or protein sequences of BCL-G, CMPK2 or LAMP3 may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating human immunodeficiency virus (HIV) in a subject comprising administering to a subject an effective amount of a pharmaceutical composition comprising a protein selected from cytidine/uridine monophosphate kinase 2, (CMPK2), its functional part thereof and its recombinant protein thereof.

2. The method of claim 1, wherein the protein is CMPK2.

3. The method of claim 1, wherein the protein is a human protein.

4. The method of claim 1, wherein the protein is prepared from a prokaryotic cell in vitro.

5. The method of claim 1, wherein the protein is prepared from a eukaryotic cell in vitro.

SEQUENCE LISTING

```
<160> NUMBER OF SEQ ID NOS: 14

<210> SEQ ID NO 1
<211> LENGTH: 3014
<212> TYPE: DNA
<213> ORGANISM: Homo sapiens

<400> SEQUENCE: 1
aacgcttcgc tttcgtttcc cgctggcgcc tggctccctc cgggtttcgt tcccgccgg      60 cgcctggctc ccgccaggtt tcgtttccga ggcggggccg agggcggcgt cgctgaggcg    120
cccatggcct tcgcccgccg gctcctgcgc gggccactgt cggggccgct gctcgggcgg    180
```

```
cgcggggtct gcgctggggc catggctccg ccgcgccgct tcgtcctgga gcttcccgac    240
tgcaccctgg ctcacttcgc cctaggcgcc gacgccccg gcgacgcaga cgccccgac     300 ccccgcctgg cggcgctgct ggggcccccg gagcgcagct actcgctgtg cgtgcccgtg    360
accccggacg ccggctgcgg ggcccgggtc cgggcggcgc ggctgcacca gcgcctgctg    420
caccagctgc gccgcggccc cttccagcgg tgccagctgc tcaggctgct ctgctactgc    480 ccggcggcc aggccggcgg cgcacagcaa ggcttcctgc tgcgcgaccc cctggatgac     540
cctgacaccc ggcaagcgct gctcgagctg ctgggcgcct gtcaggaggc accacgcccg    600
cacttgggcg agttcgaggc cgacccgcgc ggccagctgt ggcagcgcct ctgggaggtg    660
caagacggca ggcggctgca ggtgggctgc gcacaggtcg tgcccgtccc ggagcccccg    720
ctgcacccgg tggtgccaga cttgcccagt tccgtggtct tcccgaccg ggaagccgcc     780 cgggccgttt tggaggagtg tacctccttt attcctgaag cccgggcagt gcttgacctg    840
gtcgaccagt gcccaaaaca gatccagaaa ggaaagttcc aggttgttgc catcgaagga    900
ctggatgcca cgggtaaaac cacggtgacc cagtcagtgg cagattcact taaggctgtc    960
ctcttaaagt caccaccctc ttgcattggc cagtggagga agatctttga tgatgaacca   1020
actatcatta gaagagcttt ttactctttg ggcaattata ttgtggcctc cgaaatagct   1080
aaagaatctg ccaaatctcc tgtgattgta gacaggtact ggcacagcac ggccacctat   1140
gccatagcca ctgaggtgag tgggggtctc cagcacctgc ccccagccca tcaccctgtg   1200
taccagtggc cagaggacct gctcaaacct gaccttatcc tgctgctcac tgtgagtcct   1260
gaggagaggt tgcagaggct gcagggccgg ggcatggaga agaccaggga agaagcagaa   1320
cttgaggcca acagtgtgtt tcgtcaaaag gtagaaatgt cctaccagcg gatggagaat   1380
cctggctgcc atgtggttga tgccagcccc tccagagaaa aggtcctgca gacggtatta   1440
agcctaatcc agaatagttt tagtgaaccg tagttactct ggccaggtgc cacgtctaac   1500
tagattagat gttgtttgaa acatctacat ccaccatttg ttatgcagtg ttcccaaatt   1560
tctgttctac aagcatgttg tgtggcagaa aactggagac caggcatctt aattttactt   1620
cagccatcgt accctcttct gactgatgga cccgtcatca caaaggtccc tctcatcatg   1680
ttccagtgag aggccagcga ttgctttctt cctggcatag taaacatttt cttggaacat   1740
atgtttcact taatcactac caaatatctg gaagacctgt cttactcaga cagcaccagg   1800
tgtacagaag cagcagacaa gatcttccag atcagcaggg agaccccgga gcctctgctt   1860
ctcctacact ggcatgctga tgagatcgtg acatgccac attggcttct tccacatctg     1920
gttgcactcg tcatgatggg ctcgctgcat ctccctcagt cccaaattct agagccaagt   1980
gttcctgcag aggctgtcta tgtgtcctgg ctgcccaagg acactcctgc agagccattt   2040
ttgggtaagg aacacttaca agaaggcat tgatcttgtg tctgaggctc agagcccttt     2100
tgataggctt ctgagtcata tataaagaca ttcaagccaa gatgctccaa ctgcaaatat   2160
accaaccttc tctgaattat attttgctta tttatatttc ttttctttt ttctaaagta     2220 tggctctgaa tagaatgcac attttccatt gaactggatg catttcattt agccaatcca   2280
gtaatttatt tatattaatc tatacataat atgtttcctc agcataggag ctatgattca   2340
ttaattaaaa gtggagtcaa aacgctaaat gcaatgtttg ttgtgtattt tcattacaca   2400
aacttaattt gtcttgttaa ataagtacag tggatcttgg agtgggattt cttggtaaat   2460
tatcttgcac ttgaatgtct catgattaca tatgaaatcg ctttgacata tctttagaca   2520
gaaaaaagta gctgagtgag ggggaaatta tagagctgtg tgactttagg gagtaggttg   2580
```

| | | | | |
|---|---|---|---|---|
| aaccaggtga | ttacctaaaa | ttccttccag | ttcaaaggca | gataaatctg | taaattattt | 2640 |
| tatcctatct | accatttctt | aagaagacat | tactccaaaa | taattaaatt | taaggcttta | 2700 |
| tcaggtctgc | atatagaatc | ttaaattcta | ataaagtttc | atgttaatgt | cataggattt | 2760 |
| ttaaaagagc | tataggtaat | ttctatataa | tatgtgtata | ttaaaatgta | attgatttca | 2820 |
| gttgaaagta | ttttaaagct | gataaatagc | attagggttc | tttgcaatgt | ggtatctagc | 2880 |
| tgtattattg | gttttattta | ctttaaacat | tttgaaaagc | ttatactggc | agcctagaaa | 2940 |
| aacaaacaat | taatgtatct | ttatgtccct | ggcacatgaa | taaactttgc | tgtggtttac | 3000 |
| taatctatgc | tgtc | | | | | 3014 |

<210> SEQ ID NO 2
<211> LENGTH: 2961
<212> TYPE: DNA
<213> ORGANISM: Homo sapiens

<400> SEQUENCE: 2

| | | | | | | |
|---|---|---|---|---|---|---|
| aagagatgat | ttctccatcc | tgaacgtgca | gcgagcttgt | caggaagatc | ggaggtgcca | 60 |
| agtagcagag | aaagcatccc | ccagctctga | cagggagaca | gcacatgtct | aaggcccaca | 120 |
| agccttggcc | ctaccggagg | agaagtcaat | tttcttctcg | aaaatacctg | aaaaaagaaa | 180 |
| tgaattcctt | ccagcaacag | ccaccgccat | tcggcacagt | gccaccacaa | atgatgtttc | 240 |
| ctccaaactg | gcaggggggca | gagaaggacg | ctgctttcct | cgccaaggac | ttcaactttc | 300 |
| tcactttgaa | caatcagcca | ccaccaggaa | acaggagcca | accaagggca | atggggcccg | 360 |
| agaacaacct | gtacagccag | tacgagcaga | aggtgcgccc | ctgcattgac | ctcatcgact | 420 |
| ccctgcgggc | tctgggtgtg | gagcaggacc | tggccctgcc | agccatcgcc | gtcatcgggg | 480 |
| accagagctc | gggcaagagc | tctgtgctgg | aggcactgtc | aggagtcgcg | cttcccagag | 540 |
| gcagcggaat | cgtaaccagg | tgtccgctgg | tgctgaaact | gaaaaagcag | ccctgtgagg | 600 |
| catgggccgg | aaggatcagc | taccggaaca | ccgagctaga | gcttcaggac | cctggccagg | 660 |
| tggagaaaga | gatacacaaa | gcccagaacg | tcatggccgg | gaatggccgg | ggcatcagcc | 720 |
| atgagctcat | cagcctggag | atcacctccc | ctgaggttcc | agacctgacc | atcattgacc | 780 |
| ttcccggcat | caccagggtg | gctgtggaca | accagccccg | agacatcgga | ctgcagatca | 840 |
| aggctctcat | caagaagtac | atccagaggc | agcagacgat | caacttggtg | gtggttccct | 900 |
| gtaacgtgga | cattgccacc | acggaggcgc | tgagcatggc | ccatgaggtg | gacccggaag | 960 |
| gggacaggac | catcggtatc | ctgaccaaac | cagatctaat | ggcagggggc | actgagaaaa | 1020 |
| gcgtcatgaa | tgtggtgcgg | aacctcacgt | accccctcaa | gaagggctac | atgattgtga | 1080 |
| agtgccgggg | ccagcaggag | atcacaaaca | ggctgagctt | ggcagaggca | accagaaag | 1140 |
| aaattacatt | ctttcaaaca | catccatatt | tcagagttct | cctggaggag | gggtcagcca | 1200 |
| cggttccccg | actggcagaa | agacttacca | ctgaactcat | catgcatatc | caaaaatcgc | 1260 |
| tcccgttgtt | agaaggacaa | ataagggaga | gccaccagaa | ggcgaccgag | gagctgcggc | 1320 |
| gttgcggggc | tgcatccccc | agccaggagg | ccgacaagat | gttcttctta | attgagaaaa | 1380 |
| tcaagatgtt | taatcaggac | atcgaaaagt | tagtagaagg | agaagaagtt | gtaagggaga | 1440 |
| atgagacccg | tttatacaac | aaaatcagag | aggattttaa | aaactgggta | ggcatacttg | 1500 |
| caactaatac | ccaaaaagtt | aaaaatatta | tccacgaaga | agttgaaaaa | tatgaaaagc | 1560 |
| agtatcgagg | caaggagctt | ctgggatttg | tcaactacaa | gacatttgag | atcatcgtgc | 1620 |

```
atcagtacat ccagcagctg gtggagcccg cccttagcat gctccagaaa gccatggaaa    1680
ttatccagca agctttcatt aacgtggcca aaaaacattt tggcgaattt ttcaaccta     1740 accaaactgt tcagagcacg attgaagaca taaaagtgaa acacacagca aaggcagaaa    1800
acatgatcca acttcagttc agaatggagc agatggtttt ttgtcaagat cagatttaca    1860
gtgttgttct gaagaaagtc cgagaagaga tttttaaccc tctggggacg ccttcacaga    1920
atatgaagtt gaactctcat tttcccagta atgagtcttc ggtttcctcc tttactgaaa    1980
taggcatcca cctgaatgcc tacttcttgg aaaccagcaa acgtctcgcc aaccagatcc    2040
catttataat tcagtatttt atgctccgag agaatggtga ctccttgcag aaagccatga    2100
tgcagatact acaggaaaaa aatcgctatt cctggctgct tcaagagcag agtgagaccg    2160
ctaccaagag aagaatcctt aaggagagaa tttaccggct cactcaggcg cgacacgcac    2220
tctgtcaatt ctccagcaaa gagatccact gaagggcggc gatgcctgtg gttgttttct    2280
tgtgcgtact cattcattct aaggggagtc ggtgcaggat gccgcttctg ctttggggcc    2340
aaactcttct gtcactatca gtgtccatct ctactgtact ccctcagcat cagagcatgc    2400
atcaggggtc cacacaggct cagctctctc caccacccag ctcttccctg accttcacga    2460
agggatggct ctccagtcct tgggtcccgt agcacacagt tacagtgtcc taagatactg    2520
ctatcattct tcgctaattt gtatttgtat tcccttcccc ctacaagatt atgagacccc    2580 agaggggaa ggtctgggtc aaattcttct tttgtatgtc cagtctcctg cacagcacct     2640
gcagcattgt aactgcttaa taaatgacat ctcactgaac gaatgagtgc tgtgtaagtg    2700
atggagatac ctgaggctat tgctcaagcc caggccttgg acatttagtg actgttagcc    2760 ggtcccttc agatccagtg gccatgcccc ctgcttccca tggttcactg tcattgtgtt     2820
tcccagcctc tccactcccc cgccagaaag gagcctgagt gattctcttt tcttcttgtt    2880
tccctgatta tgatgagctt ccattgttct gttaagtctt gaagaggaat taataaagc     2940 aaagaaactt tttaaaaacg t                                               2961
```

<210> SEQ ID NO 3
<211> LENGTH: 252
<212> TYPE: PRT
<213> ORGANISM: Homo sapiens

<400> SEQUENCE: 3

```
Met Cys Ser Thr Ser Gly Cys Asp Leu Glu Glu Ile Pro Leu Asp Asp
1               5                   10                  15

Asp Asp Leu Asn Thr Ile Glu Phe Lys Ile Leu Ala Tyr Tyr Thr Arg
            20                  25                  30

His His Val Phe Lys Ser Thr Pro Ala Leu Phe Ser Pro Lys Leu Leu
        35                  40                  45

Arg Thr Arg Ser Leu Ser Gln Arg Gly Leu Gly Asn Cys Ser Ala Asn
    50                  55                  60

Glu Ser Trp Thr Glu Val Ser Trp Pro Cys Arg Asn Ser Gln Ser Ser
65                  70                  75                  80

Glu Lys Ala Ile Asn Leu Gly Lys Lys Ser Ser Trp Lys Ala Phe
        85                  90                  95

Phe Gly Val Val Glu Lys Glu Asp Ser Gln Ser Thr Pro Ala Lys Val
            100                 105                 110

Ser Ala Gln Gly Gln Arg Thr Leu Glu Tyr Gln Asp Ser His Ser Gln
        115                 120                 125

Gln Trp Ser Arg Cys Leu Ser Asn Val Glu Gln Cys Leu Glu His Glu
```

```
            130                 135                 140
Ala Val Asp Pro Lys Val Ile Ser Ile Ala Asn Arg Val Ala Glu Ile
145                 150                 155                 160

Val Tyr Ser Trp Pro Pro Gln Ala Thr Gln Ala Gly Gly Phe Lys
                165                 170                 175

Ser Lys Glu Ile Phe Val Thr Glu Gly Leu Ser Phe Gln Leu Gln Gly
                180                 185                 190

His Val Pro Val Ala Ser Ser Lys Lys Asp Glu Glu Gln Ile
            195                 200                 205

Leu Ala Lys Ile Val Glu Leu Leu Lys Tyr Ser Gly Asp Gln Leu Glu
            210                 215                 220

Arg Lys Asp Thr Ala Phe Ile Pro Ile Pro Leu Val Asp Thr Ser Ile
225                 230                 235                 240

Gln Gly Phe Pro Gln Asp Gly Leu Met Ala Cys Ile
                245                 250

<210> SEQ ID NO 4
<211> LENGTH: 327
<212> TYPE: PRT
<213> ORGANISM: Homo sapiens

<400> SEQUENCE: 4

Met Cys Ser Thr Ser Gly Cys Asp Leu Glu Glu Ile Pro Leu Asp Asp
1               5                   10                  15

Asp Asp Leu Asn Thr Ile Glu Phe Lys Ile Leu Ala Tyr Tyr Thr Arg
                20                  25                  30

His His Val Phe Lys Ser Thr Pro Ala Leu Phe Ser Pro Lys Leu Leu
            35                  40                  45

Arg Thr Arg Ser Leu Ser Gln Arg Gly Leu Gly Asn Cys Ser Ala Asn
        50                  55                  60

Glu Ser Trp Thr Glu Val Ser Trp Pro Cys Arg Asn Ser Gln Ser Ser
65                  70                  75                  80

Glu Lys Ala Ile Asn Leu Gly Lys Lys Ser Ser Trp Lys Ala Phe
                85                  90                  95

Phe Gly Val Val Glu Lys Glu Asp Ser Gln Ser Thr Pro Ala Lys Val
                100                 105                 110

Ser Ala Gln Gly Gln Arg Thr Leu Glu Tyr Gln Asp Ser His Ser Gln
            115                 120                 125

Gln Trp Ser Arg Cys Leu Ser Asn Val Glu Gln Cys Leu Glu His Glu
130                 135                 140

Ala Val Asp Pro Lys Val Ile Ser Ile Ala Asn Arg Val Ala Glu Ile
145                 150                 155                 160

Val Tyr Ser Trp Pro Pro Gln Ala Thr Gln Ala Gly Gly Phe Lys
                165                 170                 175

Ser Lys Glu Ile Phe Val Thr Glu Gly Leu Ser Phe Gln Leu Gln Gly
                180                 185                 190

His Val Pro Val Ala Ser Ser Lys Lys Asp Glu Glu Gln Ile
            195                 200                 205

Leu Ala Lys Ile Val Glu Leu Leu Lys Tyr Ser Gly Asp Gln Leu Glu
            210                 215                 220

Arg Lys Leu Lys Lys Asp Lys Ala Leu Met Gly His Phe Gln Asp Gly
225                 230                 235                 240

Leu Ser Tyr Ser Val Phe Lys Thr Ile Thr Asp Gln Val Leu Met Gly
                245                 250                 255
```

```
Val Asp Pro Arg Gly Glu Ser Glu Val Lys Ala Gln Gly Phe Lys Ala
            260                 265                 270

Ala Leu Val Ile Asp Val Thr Ala Lys Leu Thr Ala Ile Asp Asn His
        275                 280                 285

Pro Met Asn Arg Val Leu Gly Phe Gly Thr Lys Tyr Leu Lys Glu Asn
    290                 295                 300

Phe Ser Pro Trp Ile Gln Gln His Gly Gly Trp Lys Ile Leu Gly
305                 310                 315                 320

Ile Ser His Glu Glu Val Asp
                325

<210> SEQ ID NO 5
<211> LENGTH: 422
<212> TYPE: DNA
<213> ORGANISM: Mus musculus

<400> SEQUENCE: 5
ttaaccactg agacatctct ctaattcaag acagtcgttt ttaaattccc cacttcttga      60
gaaatccctg ttctttcttc ccataggtct ctttatccta ggacacagtc ttatctaatg     120
aataatttgg gccttgaggc tgctgcgttt ttctggtcgt gggctcagtc acatggcaga     180
ctgcctgtac ctttctaact ctcaagagtt ctgagacaaa caggggccag ctgccagcta     240
ggggagagag gagaagcctc tggttctctg taactgggc acactctaag tgcacctcat      300
actggaaaat ggaccaccat gatccacttt ttacagcttt tgccgtgagt agtacccata     360
gcctcatgca ggccagaggg caacttgcag ataccatcaa gaagagaccc tcccagggcc     420
ag                                                                    422

<210> SEQ ID NO 6
<211> LENGTH: 538
<212> TYPE: DNA
<213> ORGANISM: Drosophila melanogaster
<220> FEATURE:
<221> NAME/KEY: modified_base
<222> LOCATION: (133)..(133)
<223> OTHER INFORMATION: a, c, t, g, unknown or other
<220> FEATURE:
<221> NAME/KEY: modified_base
<222> LOCATION: (353)..(353)
<223> OTHER INFORMATION: a, c, t, g, unknown or other
<220> FEATURE:
<221> NAME/KEY: modified_base
<222> LOCATION: (364)..(364)
<223> OTHER INFORMATION: a, c, t, g, unknown or other
<220> FEATURE:
<221> NAME/KEY: modified_base
<222> LOCATION: (393)..(393)
<223> OTHER INFORMATION: a, c, t, g, unknown or other
<220> FEATURE:
<221> NAME/KEY: modified_base
<222> LOCATION: (423)..(424)
<223> OTHER INFORMATION: a, c, t, g, unknown or other
<220> FEATURE:
<221> NAME/KEY: modified_base
<222> LOCATION: (494)..(494)
<223> OTHER INFORMATION: a, c, t, g, unknown or other
<220> FEATURE:
<221> NAME/KEY: modified_base
<222> LOCATION: (515)..(515)
<223> OTHER INFORMATION: a, c, t, g, unknown or other

<400> SEQUENCE: 6
actattaggt atacatttat ctgtactttc ttttttcttt ttcatcggaa gtctttttt       60 ttgtgcgcgg aattggctcg aatgggatat gcaatttaca tataaacata atatatgcac    120
```

-continued

```
gaatatttat gtncacatga atgaaccgac atatggcagc ggttgataca tacaaattaa    180
cttaattatg cattccagta aagggtgtta tcatagatcg acggatcggt agccagtggt    240
accaggaaca tccatccaac aaatccagct aagtagaaaa taatgccac tactcgtcgc     300 cagaaatcct gctgccacag atcctgcaga tccggcagac ccatatgatt gcnaaacgcg    360
tgcnccaaga tgggagccat cacatgacct gtncgggcaa atagaaaggc cgaatagaag    420
ccnnatagcg tggtgtatat gaactggaac agtccaatca atagggcagt gctcaactcc    480
acgcctaagc tcangcgttc ggctatgttg atgcnagtgg gctactccca aaaaaagc     538
```

<210> SEQ ID NO 7
<211> LENGTH: 416
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Pro Arg Gln Leu Ser Ala Ala Ala Leu Phe Ala Ser Leu Ala
1               5                   10                  15

Val Ile Leu His Asp Gly Ser Gln Met Arg Ala Lys Ala Phe Pro Gly
            20                  25                  30

Thr Arg Asp Tyr Ser Gln Pro Thr Ala Ala Thr Val Gln Asp Ile
        35                  40                  45

Lys Lys Pro Val Gln Gln Pro Ala Lys Gln Ala Pro His Gln Thr Leu
    50                  55                  60

Ala Ala Arg Phe Met Asp Gly His Ile Thr Phe Gln Thr Ala Ala Thr
65                  70                  75                  80

Val Lys Ile Pro Thr Thr Thr Pro Ala Thr Lys Asn Thr Ala Thr
                85                  90                  95

Thr Ser Pro Ile Thr Tyr Thr Leu Val Thr Gln Ala Thr Pro Asn
            100                 105                 110

Asn Ser His Thr Ala Pro Pro Val Thr Glu Val Thr Val Gly Pro Ser
        115                 120                 125

Leu Ala Pro Tyr Ser Leu Pro Pro Thr Ile Thr Pro Ala His Thr
    130                 135                 140

Thr Gly Thr Ser Ser Ser Thr Val Ser His Thr Thr Gly Asn Thr Thr
145                 150                 155                 160

Gln Pro Ser Asn Gln Thr Thr Leu Pro Ala Thr Leu Ser Ile Ala Leu
                165                 170                 175

His Lys Ser Thr Thr Gly Gln Lys Pro Val Gln Pro Thr His Ala Pro
            180                 185                 190

Gly Thr Thr Ala Ala Ala His Asn Thr Thr Arg Thr Ala Ala Pro Ala
        195                 200                 205

Ser Thr Val Pro Gly Pro Thr Leu Ala Pro Gln Pro Ser Ser Val Lys
    210                 215                 220

Thr Gly Ile Tyr Gln Val Leu Asn Gly Ser Arg Leu Cys Ile Lys Ala
225                 230                 235                 240

Glu Met Gly Ile Gln Leu Ile Val Gln Asp Lys Glu Ser Val Phe Ser
                245                 250                 255

Pro Arg Arg Tyr Phe Asn Ile Asp Pro Asn Ala Thr Gln Ala Ser Gly
            260                 265                 270

Asn Cys Gly Thr Arg Lys Ser Asn Leu Leu Leu Asn Phe Gln Gly Gly
        275                 280                 285

| Phe | Val | Asn | Leu | Thr | Phe | Thr | Lys | Asp | Glu | Glu | Ser | Tyr | Tyr | Ile | Ser |
|---|---|---|---|---|---|---|---|---|---|---|---|---|---|---|---|
| | 290 | | | | | 295 | | | | | 300 | | | | |

| Glu | Val | Gly | Ala | Tyr | Leu | Thr | Val | Ser | Asp | Pro | Glu | Thr | Val | Tyr | Gln |
|---|---|---|---|---|---|---|---|---|---|---|---|---|---|---|---|
| 305 | | | | | 310 | | | | | 315 | | | | | 320 |

| Gly | Ile | Lys | His | Ala | Val | Val | Met | Phe | Gln | Thr | Ala | Val | Gly | His | Ser |
|---|---|---|---|---|---|---|---|---|---|---|---|---|---|---|---|
| | | | | 325 | | | | | 330 | | | | | 335 | |

| Phe | Lys | Cys | Val | Ser | Glu | Gln | Ser | Leu | Gln | Leu | Ser | Ala | His | Leu | Gln |
|---|---|---|---|---|---|---|---|---|---|---|---|---|---|---|---|
| | | | 340 | | | | | 345 | | | | | 350 | | |

| Val | Lys | Thr | Thr | Asp | Val | Gln | Leu | Gln | Ala | Phe | Asp | Phe | Glu | Asp | Asp |
|---|---|---|---|---|---|---|---|---|---|---|---|---|---|---|---|
| | | 355 | | | | | 360 | | | | | 365 | | | |

| His | Phe | Gly | Asn | Val | Asp | Glu | Cys | Ser | Ser | Asp | Tyr | Thr | Ile | Val | Leu |
|---|---|---|---|---|---|---|---|---|---|---|---|---|---|---|---|
| | 370 | | | | | 375 | | | | | 380 | | | | |

| Pro | Val | Ile | Gly | Ala | Ile | Val | Val | Gly | Leu | Cys | Leu | Met | Gly | Met | Gly |
|---|---|---|---|---|---|---|---|---|---|---|---|---|---|---|---|
| 385 | | | | | 390 | | | | | 395 | | | | | 400 |

| Val | Tyr | Lys | Ile | Arg | Leu | Arg | Cys | Gln | Ser | Ser | Gly | Tyr | Gln | Arg | Ile |
|---|---|---|---|---|---|---|---|---|---|---|---|---|---|---|---|
| | | | | 405 | | | | | 410 | | | | | 415 | |

<210> SEQ ID NO 8
<211> LENGTH: 471
<212> TYPE: DNA
<213> ORGANISM: Homo sapiens
<220> FEATURE:
<221> NAME/KEY: modified_base
<222> LOCATION: (71)..(71)
<223> OTHER INFORMATION: a, c, t, g, unknown or other
<220> FEATURE:
<221> NAME/KEY: modified_base
<222> LOCATION: (201)..(201)
<223> OTHER INFORMATION: a, c, t, g, unknown or other
<220> FEATURE:
<221> NAME/KEY: modified_base
<222> LOCATION: (273)..(273)
<223> OTHER INFORMATION: a, c, t, g, unknown or other
<220> FEATURE:
<221> NAME/KEY: modified_base
<222> LOCATION: (380)..(380)
<223> OTHER INFORMATION: a, c, t, g, unknown or other
<220> FEATURE:
<221> NAME/KEY: modified_base
<222> LOCATION: (397)..(397)
<223> OTHER INFORMATION: a, c, t, g, unknown or other
<220> FEATURE:
<221> NAME/KEY: modified_base
<222> LOCATION: (431)..(431)
<223> OTHER INFORMATION: a, c, t, g, unknown or other
<220> FEATURE:
<221> NAME/KEY: modified_base
<222> LOCATION: (437)..(437)
<223> OTHER INFORMATION: a, c, t, g, unknown or other
<220> FEATURE:
<221> NAME/KEY: modified_base
<222> LOCATION: (459)..(459)
<223> OTHER INFORMATION: a, c, t, g, unknown or other

<400> SEQUENCE: 8

| | | | | | |
|---|---|---|---|---|---|
| ggttatattt | ctgctttaat | atatagtaac | atttgaaaat | acacagatat | ccaggaaaaa | 60 |
| aaggtaaagc | ngtatgaggt | attgacagca | caactgtgtt | ttaatttggg | agttaatttg | 120 |
| gggtgttatg | taacagcaat | catacttgta | gacaaacaca | tccactagct | ctgcaaacac | 180 |
| attcaaaggt | aatagtatat | ngtacactcc | accctgtaaa | atatgtcaaa | taccccccact | 240 |
| ctacaaattc | actgtgtttc | attattttt | ttntgttttt | ataagaaaag | gggcatatca | 300 |
| ttataattca | caatccaagt | cagagtctta | atttaggtat | ggaatattac | ctgccaattt | 360 |
| tgcttctcaa | gctactttan | aaatatatat | atattcntta | aagccatttt | atggccatgg | 420 |
| gaatctaatt | natttcntaa | tgatgttggt | tgaacatgnt | acccgaaaat | g | 471 |

<210> SEQ ID NO 9
<211> LENGTH: 1930
<212> TYPE: DNA
<213> ORGANISM: Homo sapiens

<400> SEQUENCE: 9

```
ttcaggctga gtcctaaacc tgaagaaagt ttagagcctg gggctctaaa ctacctgagt      60
ctttccaaac gacaagccaa gaagacctgt tgaaagtttc ctcttaagtt tcgtggagag     120
agactcaggt atagaaatat ccttactgcc acctgacctg aagcagaaga aatcacagac     180
agcttccaga ccaggcccaa catgtgtagc accagtgggt gtgacctgga agaaatcccc     240
ctagatgatg atgacctaaa caccatagaa ttcaaaatcc tcgcctacta caccagacat     300
catgtcttca agagcacccc tgctctcttc tcaccaaagc tgctgagaac aagaagtttg     360
tcccagaggg gcctggggaa ttgttcagca atgagtcat ggacagaggt gtcatggcct      420
tgcagaaatt cccaatccag tgagaaggcc ataaacttg gcaagaaaaa gtcttcttgg       480
aaagcattct ttggagtagt ggagaaggaa gattcgcaga gcacgcctgc caaggtctct     540
gctcagggtc aaaggacgtt ggaataccaa gattcgcaca gccagcagtg gtccaggtgt     600
ctttctaacg tggagcagtg cttggagcat gaagctgtgg accccaaagt catttccatt     660
gccaaccgag tagctgaaat tgtttactcc tggccaccac cacaagcgac ccaggcagga    720
ggcttcaagt ccaaagagat ttttgtaact gagggtctct ccttccagct ccaaggccac    780
gtgcctgtag cttcaagttc taagaaagat gaagaagaac aaatactagc caaaattgtt    840
gagctgctga atattcagg agatcagttg gaaagaaagc tgaagaaaga taaggctttg    900
atgggccact tccaggatgg gctgtcctac tctgttttca agaccatcac agaccaggtc    960
ctaatgggtg tggaccccag gggagaatca gaggtcaaag ctcagggctt taaggctgcc   1020
cttgtaatag acgtcacggc caagctcaca gctattgaca accacccgat gaacagggtc   1080
ctgggctttg gcaccaagta cctgaaagag aacttctcgc catggatcca gcagcacggt   1140
ggatgggaaa aaatacttgg gatatcacat gaagaagtag actgaaatat cagatttgtc   1200
atcaggaata ctctttgtct actgtggtcc tgtgcacgtt ggcctcagat ggactacagg   1260
agattacaac gtacaaggca gatggagcat tgacgttttc aaaaccatta ttcctgtgac   1320
tggagaggca tcaggagagg tctcgttcgt ctccagctca taaatgtag cagcatcatc    1380
cttgacagtg atgtttttca ggccctccat tgagaacctg aggaaatctg taaagataag   1440
tggtgatgtt gtttcaaacg ttcagaacag ataccatcat cctgcctttg ttagctgctg   1500
tagggaaagt gcgttacaga tgtctgctga cctcacaaga gtgaaaagat aaactgtgca   1560
tgtgtttcca cttccgtttc tagtactatt tatttttaaa ctacacttgg ggtggcctaa   1620
tacctaggaa gatgttgcta ttcacgttag taaacagcct aaagaaactc ttaggtttac   1680
tgctacatcc atttgtttgg agaggtaact gttgtctgtg cctttttgaa aaacttccat   1740
ttggtacaaa attttactc caacaccccc tcaacccttt tctcagggac cacacctctt    1800
cttcccaagg tccctgggac ttcctcattc tttgtggtag tacaatgatt ggtagcaggt   1860
aaaataaata catagaaaga ctactgtcaa aaaaaaaaaa aaaaaaaaa aaaaaaaaa     1920
aaaaaaaaaa                                                           1930
```

<210> SEQ ID NO 10
<211> LENGTH: 2039
<212> TYPE: DNA

<213> ORGANISM: Homo sapiens

<400> SEQUENCE: 10

```
aatgacatga cagccattcc gtggccaggg acaccactgc ccaagctgga gaccacgagg      60
attcagggac tgaagccagc atgggaattc ctggtttgag atcagagtcc tgagtacctc     120
gtgggaactt gggcactcat ccgcaggagg tctagacccc cagagaattc cttgagtcta     180
aggcacaggc caacatgtg tagcaccagt gggtgtgacc tggaagaaat cccctagat       240
gatgatgacc taaacaccat agaattcaaa atcctcgcct actacaccag acatcatgtc     300
ttcaagagca cccctgctct cttctcacca aagctgctga gaacaagaag tttgtcccag     360
aggggcctgg ggaattgttc agcaaatgag tcatggacag aggtgtcatg gccttgcaga     420
aattcccaat ccagtgagaa ggccataaac cttggcaaga aaaagtcttc ttggaaagca     480
ttctttggag tagtggagaa ggaagattcg cagagcacgc ctgccaaggt ctctgctcag     540
ggtcaaagga cgttggaata ccaagattcg cacagccagc agtggtccag gtgtctttct     600
aacgtggagc agtgcttgga gcatgaagct gtggacccca aagtcatttc cattgccaac     660
cgagtagctg aaattgttta ctcctggcca ccaccacaag cgacccaggc aggaggcttc     720
aagtccaaag agatttttgt aactgagggt ctctccttcc agctccaagg ccacgtgcct     780
gtagcttcaa gttctaagaa agatgaagaa gaacaaatac tagccaaaat tgttgagctg     840
ctgaaatatt caggagatca gttggaaaga aaggacactg ccttcatccc cattcccttg     900
gttgacacca gcatccaggg ttttccacag gatggtttga tggcctgcat ttgagctaaa     960
gaatgaactt ctgtctgcct cgtggagcca agctactgta ctgagtgctt attcttttgt    1020
acacagctga agaaagataa ggctttgatg ggccacttcc aggatgggct gtcctactct    1080
gttttcaaga ccatcacaga ccaggtccta atgggtgtgg accccagggg agaatcagag    1140
gtcaaagctc agggctttaa ggctgccctt gtaatagacg tcacggccaa gctcacagct    1200
attgacaacc acccgatgaa cagggtcctg gctttggca ccaagtacct gaaagagaac     1260
ttctcgccat ggatccagca gcacggtgga tgggaaaaaa tacttgggat atcacatgaa    1320
gaagtagact gaaatatcag atttgtcatc aggaatactc tttgtctact gtggtcctgt    1380
gcacgttggc ctcagatgga ctacaggaga ttacaacgta caaggcagat ggagcattga    1440
cgttttcaaa accattattc ctgtgactgg agaggcatca ggagaggtct cgttcgtctc    1500
cagctcataa aatgtagcag catcatcctt gacagtgatg ttttttcaggc cctccattga    1560
gaacctgagg aaatctgtaa agataagtgg tgatgttgtt tcaaacgttc agaacagata    1620
ccatcatcct gcctttgtta gctgctgtag ggaaagtgcg ttacagatgt ctgctgacct    1680
cacaagagtg aaaagataaa ctgtgcatgt gtttccactt ccgtttctag tactatttat    1740
ttttaaacta cacttggggt ggcctaatac ctaggaagat gttgctattc acgttagtaa    1800
acagcctaaa gaaactctta ggtttactgc tacatccatt tgtttggaga ggtaactgtt    1860
gtctgtgcct ttttgaaaaa cttccatttg gtacaaaatt tttactccaa cacccctca    1920
acccttttct cagggaccac acctcttctt cccaaggtcc ctgggacttc ctcattcttt    1980
gtggtagtac aatgattggt agcaggtaaa ataaatacat agaaagacta ctgtcaaaa    2039
```

<210> SEQ ID NO 11
<211> LENGTH: 1241
<212> TYPE: DNA
<213> ORGANISM: Homo sapiens

<400> SEQUENCE: 11

```
aacgcttcgc tttcgtttcc cgctggcgcc tggctccctc cgggtttcgt ttcccgccgg    60
cgcctggctc ccgccaggtt tcgtttccga ggcggggccg agggcggcgt cgctgaggcg   120
cccatggcct tcgcccgccg gctcctgcgc gggccactgt cggggccgct gctcgggcgg   180
cgcggggtct gcgctgggc catggctccg ccgcgccgct tcgtcctgga gcttcccgac    240
tgcaccctgg ctcacttcgc cctaggcgcc gacgccccg gcgacgcaga cgccccgac     300 ccccgcctgg cggcgctgct ggggcccccg gagcgcagct actcgctgtg cgtgcccgtg   360
accccggacg ccggctgcgg ggcccgggtc cgggcggcgc ggctgcacca gcgcctgctg   420
caccagctgc gccgcggccc cttccagcgg tgccagctgc tcaggctgct ctgctactgc   480
ccgggcggcc aggccggcgg cgcacagcaa ggcttcctgc tgcgcgaccc cctggatgac   540
cctgacaccc ggcaagcgct gctcgagctg ctgggcgcct gtcaggaggc accacgcccg   600
cacttgggcg agttcgaggc cgacccgcgc ggccagctgt ggcagcgcct ctgggaggtg   660
caagacggca ggcggctgca ggtgggctgc gcacaggtcg tgcccgtccc ggagcccccg   720
ctgcacccgg tggtgccaga cttgcccagt tccgtggtct tcccggaccg ggaagccgcc   780
cgggccgttt tggaggagtg tacctccttt attcctgaag cccgggcagt gcttgacctg   840
gtcgaccagt gcccaaaaca gatccagaaa ggaaagttcc aggttgttgc catcgaagga   900
ctggatgcca cgggtaaaac cacggtgacc cagtcagtgg cagattcact taaggctgtc   960
ctcttaaagt caccaccctc ttgcattggc cagtggagga agatctttga tgatgaacca   1020
actatcatta gaagagcttt ttactctttg ggcaattata ttgtggcctc cgaaatagct   1080
aaagaatctg ccaaatctcc tgtgattgta gacaggtccc agctgggagg aaccttatac   1140
catccttctc tccacctgct cggcagtgaa gtttgtggga ctggaatctt ggattcatca   1200
cactcgagtc aaggcctgga atgaccctg acatcccaga a                        1241
```

<210> SEQ ID NO 12
<211> LENGTH: 2176
<212> TYPE: DNA
<213> ORGANISM: Homo sapiens

<400> SEQUENCE: 12

```
aacgcttcgc tttcgtttcc cgctggcgcc tggctccctc cgggtttcgt ttcccgccgg    60
cgcctggctc ccgccaggtt tcgtttccga ggcggggccg agggcggcgt cgctgaggcg   120
cccatggcct tcgcccgccg gctcctgcgc gggccactgt cggggccgct gctcgggcgg   180
cgcggggtct gcgctgggc catggctccg ccgcgccgct tcgtcctgga gcttcccgac    240
tgcaccctgg ctcacttcgc cctaggcgcc gacgccccg gcgacgcaga cgccccgac     300 ccccgcctgg cggcgctgct ggggcccccg gagcgcagct actcgctgtg cgtgcccgtg   360
accccggacg ccggctgcgg ggcccgggtc cgggcggcgc ggctgcacca gcgcctgctg   420
caccagctgc gccgcggccc cttccagcgg tgccagctgc tcaggctgct ctgctactgc   480
ccgggcggcc aggccggcgg cgcacagcaa ggcttcctgc tgcgcgaccc cctggatgac   540
cctgacaccc ggcaagcgct gctcgagctg ctgggcgcct gtcaggaggc accacgcccg   600
cacttgggcg agttcgaggc cgacccgcgc ggccagctgt ggcagcgcct ctgggaggtg   660
caagacggca ggcggctgca ggtgggctgc gcacaggtcg tgcccgtccc ggagcccccg   720
ctgcacccgg tggtgccaga cttgcccagt tccgtggtct tcccggaccg ggaagccgcc   780
cgggccgttt tggaggagtg tacctccttt attcctgaag cccgggcagt gcttgacctg   840
```

```
gtcgaccagt gcccaaaaca gatccagaaa ggaaagttcc aggttgttgc catcgaagga     900
ctggatgcca cgggtaaaac cacggtgacc cagtcagtgg cagattcact taaggctgtc     960
ctcttaaagt caccaccctc ttgcattggc cagtggagga agatctttga tgatgaacca    1020
actatcatta agagcttt ttactctttg ggcaattata ttgtggcctc cgaaatagct    1080
aaagaatctg ccaaatctcc tgtgattgta gacaggtact ggcacagcac ggccacctat    1140
gccatagcca ctgaggtgag tggggtctc cagcacctgc ccccagccca tcaccctgtg    1200
taccagtggc cagaggacct gctcaaacct gaccttatcc tgctgctcac tgtgagtcct    1260
gaggagaggt tgcagaggct gcagggccgg ggcatggaga agaccaggga agaagcagaa    1320
cttgaggcca acagtgtgtt tcgtcaaaag taggtgtccc agtgcaatgc aatgtgagcg    1380
gcaggcattc ctgaagggag atgaaccact ggcactggct ttaggattgt gaggaagtga    1440
tattgttttc agttttcaaa cacaagagac aacatcctct aagttacttc agccccttcc    1500
aatgggcttg tcaccacagg gctgcagcat tgttatctta agcaaaggt catcggacta    1560 gggatcagac cctgccactg atcctggctg tgctaggagc agctgcacct gggtaagaca    1620
gtaagtgtct ctgtgcctca gtttccccag tcatagtata atcacacaga gcactagata    1680
acgagctcat agtaacatct acctattaga tgcttcccgt gtgtcaggca ttttactgat    1740
gttatgtcat ccttgtgagg aaaacattag ccgtatttta cagtttacaa ctttaaggct    1800
caaaggatta agtgatttgt ctaaatgtac ataactattc actagtaaaa ccgggattaa    1860
aatctttctg attttgcagc cagtgttttt gttttaatta gaaagttata aacacgactg    1920
cagaagagag tctggccagg cctcctgcct catgactgag tatgaatcag ttctacacca    1980
ctgcctttaa aaactgaagc agaaatattt tctctaactg aacaatgata gccctgttat    2040
cataacatag taatgttata aataatggta gctgctgtgg gtaaagatat tatgttaagc    2100
aatttacttg tattaattcc attaaacttc agtgaacatt tgcaaggaaa aaaaaaaaa    2160 aaaaaaaaaa aaaaaa                                                   2176

<210> SEQ ID NO 13
<211> LENGTH: 2426
<212> TYPE: DNA
<213> ORGANISM: Homo sapiens

<400> SEQUENCE: 13
aggcagttac actgttaggc agcaacagtg ctgatgctgg actgtggcag gcagagggtg      60
ctatcctgac acacttcacc ttagtgcagg aaacttcaat ttggtggaag aaaggcgatt     120
tcgaggtgcc aatctgggcg acacttccca gttggagagt cagcaaaagg gagagggcaa     180
ttccaagaag agggaaaagc ttgtgcacag tgtacctcct ttattcctga gcccgggca     240 gtgcttgacc tggtcgacca gtgcccaaaa cagatccaga aggaaagtt ccaggttgtt     300 gccatcgaag gactggatgc cacgggtaaa accacggtga cccagtcagt ggcagattca     360
cttaaggctg tcctcttaaa gtcaccaccc tcttgcattg ccagtggag gaagatcttt     420 gatgatgaac caactatcat tagaagagct ttttactctt tgggcaatta tattgtggcc     480
tccgaaatag ctaaagaatc tgccaaatct cctgtgattg tagacaggta ctggcacagc     540
acggccacct atgccatagc cactgaggtg agtgggggtc tccagcacct gcccccagcc     600
catcaccctg tgtaccagtg gccagaggac ctgctcaaac ctgaccttat cctgctgctc     660
actgtgagtc ctgaggagag gttgcagagg ctgcagggcc ggggcatgga gaagaccagg     720
gaagaagcag aacttgaggc caacagtgtg tttcgtcaaa aggtagaaat gtcctaccag     780
```

```
cggatggaga atcctggctg ccatgtggtt gatgccagcc cctccagaga aaaggtcctg    840
cagacggtat taagcctaat ccagaatagt tttagtgaac cgtagttact ctggccaggt    900
gccacgtcta actagattag atgttgtttg aaacatctac atccaccatt tgttatgcag    960
tgttcccaaa tttctgttct acaagcatgt tgtgtggcag aaaactggag accaggcatc   1020
ttaattttac ttcagccatc gtaccctctt ctgactgatg gacccgtcat cacaaaggtc   1080
cctctcatca tgttccagtg agaggccagc gattgctttc ttcctggcat agtaaacatt   1140
ttcttggaac atatgtttca cttaatcact accaaatatc tggaagacct gtcttactca   1200
gacagcacca ggtgtacaga agcagcagac aagatcttcc agatcagcag ggagaccccg   1260
gagcctctgc ttctcctaca ctggcatgct gatgagatcg tgacatgccc acattggctt   1320
cttccacatc tggttgcact cgtcatgatg ggctcgctgc atctccctca gtcccaaatt   1380
ctagagccaa gtgttcctgc agaggctgtc tatgtgtcct ggctgcccaa ggacactcct   1440
gcagagccat ttttgggtaa ggaacactta caaagaaggc attgatcttg tgtctgaggc   1500
tcagagccct tttgataggc ttctgagtca tatataaaga cattcaagcc aagatgctcc   1560
aactgcaaat ataccaacct ctctgaatt atattttgct tatttatatt tcttttcttt    1620
ttttctaaag tatggctctg aatagaatgc acattttcca ttgaactgga tgcatttcat   1680
ttagccaatc cagtaattta tttatattaa tctatacata atatgtttcc tcagcatagg   1740
agctatgatt cattaattaa aagtggagtc aaaacgctaa atgcaatgtt tgttgtgtat   1800
tttcattaca caaacttaat ttgtcttgtt aaataagtac agtggatctt ggagtgggat   1860
ttcttggtaa attatcttgc acttgaatgt ctcatgatta catatgaaat cgctttgaca   1920
tatctttaga cagaaaaaag tagctgagtg aggggggaaat tatagagctg tgtgactttta  1980 gggagtaggt tgaaccaggt gattacctaa aattccttcc agttcaaagg cagataaatc   2040
tgtaaattat tttatcctat ctaccatttc ttaagaagac attactccaa ataattaaa    2100 tttaaggctt tatcaggtct gcatatagaa tcttaaattc taataaagtt tcatgttaat   2160
gtcataggat tttaaaaga gctataggta atttctatat aatatgtgta tattaaaatg    2220
taattgattt cagttgaaag tattttaaag ctgataaata gcattagggt tctttgcaat   2280
gtggtatcta gctgtattat tggttttatt tactttaaac attttgaaaa gcttatactg   2340
gcagcctaga aaaacaaaca attaatgtat ctttatgtcc ctggcacatg aataaacttt   2400
gctgtggttt actaatctat gctgtc                                        2426
```

<210> SEQ ID NO 14
<211> LENGTH: 2426
<212> TYPE: DNA
<213> ORGANISM: Homo sapiens

<400> SEQUENCE: 14

```
aggcagttac actgttaggc agcaacagtg ctgatgctgg actgtggcag gcagagggtg     60
ctatcctgac acacttcacc ttagtgcagg aaacttcaat ttggtggaag aaaggcgatt    120
tcgaggtgcc aatctgggcg acacttccca gttggagagt cagcaaaagg gagagggcaa    180
ttccaagaag agggaaaagc ttgtgcacag tgtacctcct ttattcctga agcccgggca    240
gtgcttgacc tggtcgacca gtgcccaaaa cagatccaga aggaaagtt ccaggttgtt     300 gccatcgaag gactggatgc cacgggtaaa accacggtga cccagtcagt ggcagattca    360
cttaaggctg tcctcttaaa gtcaccaccc tcttgcattg ccagtgggag gaagatcttt    420
```

```
gatgatgaac caactatcat tagaagagct ttttactctt tgggcaatta tattgtggcc      480
tccgaaatag ctaaagaatc tgccaaatct cctgtgattg tagacaggta ctggcacagc      540
acggccacct atgccatagc cactgaggtg agtgggggtc tccagcacct gcccccagcc      600
catcaccctg tgtaccagtg gccagaggac ctgctcaaac ctgaccttat cctgctgctc      660
actgtgagtc ctgaggagag gttgcagagg ctgcagggcc ggggcatgga aagaccagg       720 gaagaagcag aacttgaggc aacagtgtg tttcgtcaaa aggtagaaat gtcctaccag        780
cggatggaga atcctggctg ccatgtggtt gatgccagcc cctccagaga aaggtcctg       840 cagacggtat taagcctaat ccagaatagt tttagtgaac cgtagttact ctggccaggt      900
gccacgtcta actagattag atgttgtttg aaacatctac atccaccatt tgttatgcag      960
tgttcccaaa tttctgttct acaagcatgt tgtgtggcag aaaactggag accaggcatc     1020
ttaattttac ttcagccatc gtaccctctt ctgactgatg gacccgtcat cacaaaggtc     1080
cctctcatca tgttccagtg agaggccagc gattgctttc ttcctggcat agtaaacatt     1140
ttcttggaac atatgtttca cttaatcact accaaatatc tggaagacct gtcttactca     1200
gacagcacca ggtgtacaga agcagcagac aagatcttcc agatcagcag ggagaccccg     1260
gagcctctgc ttctcctaca ctggcatgct gatgagatcg tgacatgccc acattggctt     1320
cttccacatc tggttgcact cgtcatgatg ggctcgctgc atctccctca gtcccaaatt     1380
ctagagccaa gtgttcctgc agaggctgtc tatgtgtcct ggctgcccaa ggacactcct     1440
gcagagccat ttttgggtaa ggaacactta caaagaaggc attgatcttg tgtctgaggc     1500
tcagagccct tttgataggc ttctgagtca tatataaaga cattcaagcc aagatgctcc     1560
aactgcaaat ataccaacct tctctgaatt atattttgct tatttatatt tcttttcttt     1620
ttttctaaag tatggctctg aatagaatgc acattttcca ttgaactgga tgcatttcat     1680
ttagccaatc cagtaattta tttatattaa tctatacata atatgtttcc tcagcatagg     1740
agctatgatt cattaattaa aagtggagtc aaaacgctaa atgcaatgtt tgttgtgtat     1800
tttcattaca caaacttaat ttgtcttgtt aaataagtac agtggatctt ggagtgggat     1860
ttcttggtaa attatcttgc acttgaatgt ctcatgatta catatgaaat cgctttgaca     1920
tatctttaga cagaaaaaag tagctgagtg aggggggaaat tatagagctg tgtgactta     1980 gggagtaggt tgaaccaggt gattacctaa aattccttcc agttcaaagg cagataaatc     2040
tgtaaattat tttatcctat ctaccatttc ttaagaagac attactccaa aataattaaa     2100
tttaaggctt tatcaggtct gcatatagaa tcttaaattc taataaagtt tcatgttaat     2160
gtcataggat ttttaaaaga gctataggta atttctatat aatatgtgta tattaaaatg     2220
taattgattt cagttgaaag tattttaaag ctgataaata gcattagggt tctttgcaat     2280
gtggtatcta gctgtattat tggttttatt tactttaaac attttgaaaa gcttatactg     2340
gcagcctaga aaaacaaaca attaatgtat ctttatgtcc ctggcacatg aataaacttt     2400
gctgtggttt actaatctat gctgtc                                          2426
```